United States Patent
Murakata et al.

(10) Patent No.: US 9,163,051 B2
(45) Date of Patent: Oct. 20, 2015

(54) CRYSTAL OF SPIROKETAL DERIVATIVES AND PROCESS FOR PREPARATION OF SPIROKETAL DERIVATIVES

(71) Applicant: Chugai Seiyaku Kabushiki Kaisha, Tokyo (JP)

(72) Inventors: Masatoshi Murakata, Tokyo (JP); Takuma Ikeda, Tokyo (JP); Nobuaki Kimura, Tokyo (JP); Akira Kawase, Tokyo (JP); Masahiro Nagase, Tokyo (JP); Keisuke Yamamoto, Shizuoka (JP); Noriyuki Takata, Shizuoka (JP); Shinichi Yoshizaki, Shizuoka (JP); Koji Takano, Shizuoka (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/034,880

(22) Filed: Sep. 24, 2013

(65) Prior Publication Data
US 2014/0024817 A1 Jan. 23, 2014

Related U.S. Application Data

(62) Division of application No. 13/000,208, filed as application No. PCT/JP2009/061226 on Jun. 19, 2009, now Pat. No. 8,569,520.

(30) Foreign Application Priority Data

Jun. 20, 2008 (JP) ................. 2008/162073

(51) Int. Cl.
| | | |
|---|---|---|
| C07D 313/00 | (2006.01) |
| C07D 315/00 | (2006.01) |
| C07H 19/01 | (2006.01) |
| C07D 493/10 | (2006.01) |
| C07H 7/04 | (2006.01) |
| C07H 13/04 | (2006.01) |
| C07H 23/00 | (2006.01) |

(52) U.S. Cl.
CPC .............. *C07H 19/01* (2013.01); *C07D 493/10* (2013.01); *C07H 7/04* (2013.01); *C07H 13/04* (2013.01); *C07H 23/00* (2013.01)

(58) Field of Classification Search
CPC ...................................................... C07H 19/01
USPC ................................................. 549/344, 417
See application file for complete search history.

(56) References Cited

U.S. PATENT DOCUMENTS

| | | | |
|---|---|---|---|
| 4,521,431 A | 6/1985 | Crookes | |
| 4,894,459 A | 1/1990 | Bod et al. | |
| 2007/0275907 A1* | 11/2007 | Chen et al. | ............... 514/23 |
| 2009/0030006 A1 | 1/2009 | Kobayashi et al. | |

FOREIGN PATENT DOCUMENTS

| | | |
|---|---|---|
| EP | 2048153 A1 | 4/2009 |
| JP | 5791983 A | 6/1982 |
| JP | 7316141 A | 12/1995 |
| JP | 200044534 A | 2/2000 |
| WO | 9302084 A1 | 2/1993 |
| WO | 9620197 A1 | 7/1996 |
| WO | WO 2006080421 A1 | 8/2006 |
| WO | 2007070984 A1 | 6/2007 |
| WO | 2007140191 A2 | 12/2007 |
| WO | WO 2008013280 A1 | 1/2008 |

OTHER PUBLICATIONS

Dorwald F. A. Side Reactions in Organic Synthesis, 2005, Wiley: VCH, Weinheim p. IX of Preface p. 1-15.
Nishiyama et al. Journal of Organic Chemistry (1992), 57(1), 407-10.
Ian et al Synthetic Communications (2001), 31(15), 2323-2327.
The Chemical Society of Japan Shin Jikken Kagaku Koza 1 Kihon Sosa I, Jun. 10, 1985, pp. 318-322.
"The Chemical Society of Japan", Shin Jikken Kagaku Koza 1 Kihon Sosa I, 6th print, Maruzen Co., Ltd., Jun. 10, 1985, pp. 318-322.

* cited by examiner

Primary Examiner — Nizal Chandrakumar
(74) Attorney, Agent, or Firm — Browdy and Neimark, PLLC

(57) ABSTRACT

The present invention provides a process for preparing a spiroketal derivative, via an intermediate represented by Formula (VI):

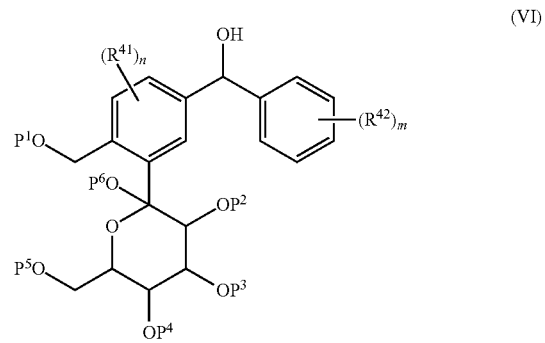

wherein variable groups and numbers are as defined in the specification, which can be produced from dihalobenzene derivatives in one pot reaction.

7 Claims, 5 Drawing Sheets

CRYSTAL OF SPIROKETAL DERIVATIVES AND PROCESS FOR PREPARATION OF SPIROKETAL DERIVATIVES

TECHNICAL FIELD

The present invention relates to a process for preparing spiroketal derivatives, to an intermediate compound useful for preparing spiroketal derivatives and to a crystalline substance of spiroketal derivatives.

BACKGROUND ART

A spiroketal derivative having a certain structure is known as being useful for preventing or treating diabetes (refer to Patent Documents 1 to 4). For example, WO 2006/080121 A1 (Patent Document 1) discloses a compound represented by Formula (A):

[Formula 1]

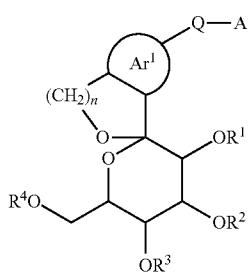

(A)

and use thereof as an anti-diabetes drug.

Patent Document 1 also discloses a process for preparing the compound represented by Formula (A). Scheme 3 (page 24 of Patent Document 1) indicates a preparation process, in which a dibromobenzene derivative is treated with an alkyllithium reagent followed by coupling with a lactone, and after conversion to a tin compound a coupling reaction in the presence of a palladium catalyst is carried) give the desired compound.

Further, WO 2007/140191 A2 (Patent Document 2) and US Patent Application publication corresponding thereto: US 2007/0275907 A1 (Patent Document 3) disclose a preparation process in Scheme 4 (pages 24 and 25 and FIG. 4 of Patent Document 2), in which a dihalotoluene derivative is treated with n-BuLi, s-BuLi, t-BuLi, Mg or the like followed by coupling with a lactone, and a tin compound obtained after several steps is subjected to coupling with a benzyl halide derivative to give a desired compound.

Moreover, Patent Document 1 discloses a compound represented by Formula (B):

[Formula 2]

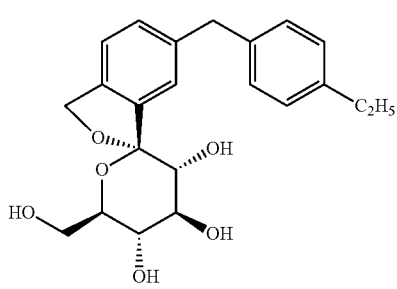

(B)

with stating that the compound has an excellent inhibitory activity against SGLT2.

CITATION LIST

Patent Document

| | |
|---|---|
| Patent Document 1: | WO 2006/080421 A1 |
| Patent Document 2: | WO 2007/140191 A2 |
| Patent Document 3: | US 2007/0275907 A1 |
| Patent Document 4: | WO 2008/013280 A1 |

SUMMARY OF INVENTION

Technical Problem

As stated above, Scheme 3 in Patent Document 1 and Scheme 4 in Patent Document 2 disclose a scheme for preparing a compound having a spiroketal structure from a dihalobenzene derivative. However, the synthetic process using a tin compound needs cumbersome operations, and necessarily requires a step for carefully removing a tin compound, which may exist as an impurity. Therefore, these processes are not suitable for industrial production. Further, these patent documents fail to disclose any specific example regarding the preparation schemes. Actually, an efficient and convenient industrial process for preparation of compounds represented by Formulae (A) and (B), which are used as an active ingredient of medicament, has not been known.

Further, there has been no report regarding existence of crystal of the compound represented by Formula (B) having excellent inhibitory activity against SGLT2.

An object of the present invention is to provide an efficient and convenient process, which is suitable for industrial production, for preparing spiroketal derivatives used as an active ingredient of medicament, and to provide a useful synthetic intermediate, and to provide a crystal having excellent properties in storage stability, ease in handling in formulation process and the like.

Solution To Problem

The present inventors have conducted intensive studies to achieve the above-mentioned objects and consequently have found a method for regioselective metalation of one of plural halogen atoms on a benzene ring. The inventors have also found a coupling reaction proceeds smoothly via a novel organometal compound as an intermediate, which can be readily prepared. Further, the inventors have found that two consecutive coupling reactions can be carried out as an efficient one-pot reaction. Consequently, the present invention has been completed. The present invention provides a process for preparing a desired spiroketal derivative without using heavy metal such as tin or an organotransition metal complex in the carbon-carbon bond forming reactions. A process using heavy metal such as tin or an organotransition metal complex necessarily requires a step for carefully removing these reagents, which may exist as an impurity, while the process of the present invention does not need such a step. Therefore, the process is superior particularly as an industrial process for a medicinal material.

In addition, the inventors have found a crystal form of the compound represented by Formula (I) and a process for preparing the crystal form. The inventors have also found that the crystal form has excellent properties as a medicament or a medicinal material. Consequently, the present invention has been completed.

According to one aspect of the present invention, there is provided a process for preparing a compound represented by Formula (I):

[Formula 3]

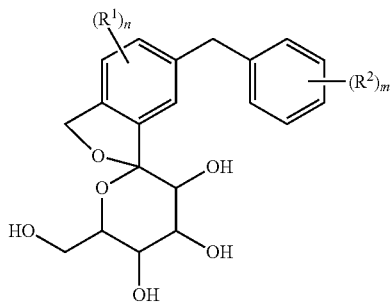

(I)

wherein n is an integer selected from 0 to 3, m is an integer selected from 0 to 5;

$R^1$ and $R^2$ are independently selected from $C_{1-10}$alkyl optionally substituted with one or more Ra, $C_{3-10}$cycloalkyl optionally substituted with one or more Ra, $C_{2-10}$alkenyl optionally substituted with one or more Ra, $C_{3-10}$cycloalkenyl optionally substituted with one or more Ra, $C_{2-10}$alkynyl optionally substituted with one or more Ra, aryl optionally substituted with one or more Ra, saturated, partially unsaturated or unsaturated heterocyclyl optionally substituted with one or more Ra, cyano, a halogen atom, nitro, mercapto, —$OR^3$, —$NR^4R^5$, —$S(O)_pR^6$, —$S(O)_qNR^7R^8$, —$C(=O)R^{35}$, —$CR^{36}=NOR^{37}$, —$C(=O)OR^9$, —$C(=O)NR^{10}R^{11}$, and —$SiR^{12}R^{13}R^{14}$; wherein when n is 2 or more, each of $R^1$ may be the same or different; when m is 2 or more, each of $R^2$ may be the same or different; or two $R^1$ on adjacent carbon atoms, together with the carbon atoms to which they are attached, may form a carbocyclic ring or a heterocyclic ring, which fuses the benzene ring; and two $R^2$ on adjacent carbon atoms, together with the carbon atoms to which they are attached, may form a carbocyclic ring or a heterocyclic ring, which fuses the benzene ring;

p is an integer selected from 0 to 2; q is an integer selected from 1 and 2;

$R^3$ is a hydrogen atom, $C_{1-10}$alkyl, $C_{3-10}$cycloalkyl, $C_{2-10}$alkenyl, $C_{3-10}$cycloalkenyl, $C_{2-10}$alkynyl, aryl, heteroaryl, —$SiR^{12}R^{13}R^{14}$, or —$C(=O)R^{15}$;

$R^4$ and $R^5$ are independently selected from a hydrogen atom, hydroxy, $C_{1-10}$alkyl, $C_{3-10}$cycloalkenyl, $C_{1-10}$alkoxy, aryl, heteroaryl, —$SiR^{12}R^{13}R^{14}$, and —$C(=O)R^{15}$;

$R^6$ is $C_{1-10}$alkyl, $C_{3-10}$cycloalkyl, aryl, or heteroaryl, wherein when p is 0, $R^6$ may further be —$SiR^{12}R^{13}R^{14}$, or —$C(=O)R^{15}$;

$R^7$, $R^8$, $R^{10}$ and $R^{11}$ are independently selected from a hydrogen atom, $C_{1-10}$alkyl, $C_{3-10}$cycloalkyl, aryl, heteroaryl, —$SiR^{12}R^{13}R^{14}$, and —$C(=O)R^{15}$;

$R^9$ is a hydrogen atom, $C_{1-10}$alkyl, $C_{3-10}$cycloalkyl, aryl, heteroaryl, or —$SiR^{12}R^{13}R^{14}$;

Ra are independently selected from $C_{3-10}$cycloalkyl, $C_{2-10}$alkenyl, $C_{3-10}$cycloalkenyl, $C_{2-10}$alkynyl, aryl, heteroaryl, hydroxy, a halogen atom, —$NR^{21}R^{22}$, —$OR^{38}$, —$SR^{26}$, —$S(O)_2R^{27}$, —$SiR^{23}R^{24}R^{25}$, carboxy, —$C(O)NR^{28}R^{29}$, —$C(=O)R^{30}$, —$CR^{31}=NOR^{32}$, cyano, and —$S(O)_rNR^{33}R^{34}$;

r is an integer selected from 1 and 2;

$R^{12}$, $R^{13}$, $R^{14}$, $R^{23}$, $R^{24}$, and $R^{25}$ are independently selected from $C_{1-10}$alkyl and aryl;

$R^{15}$ and $R^{30}$ are independently selected from a hydrogen atom, $C_{1-10}$alkyl, $C_{3-10}$cycloalkyl, $C_{1-10}$alkoxy, $C_{1-10}$alkylamino, di($C_{1-10}$alkyl)amino, $C_{1-10}$alkylthio, aryl, and heteroaryl;

$R^{21}$, $R^{22}$, $R^{28}$, $R^{29}$, $R^{33}$ and $R^{34}$ are independently selected from a hydrogen atom, hydroxy, $C_{1-10}$alkyl, $C_{3-10}$cycloalkyl, $C_{1-10}$alkoxy, aryl, heteroaryl, —$SiR^{23}R^{24}R^{25}$, and —$C(=O)R^{30}$; $R^{26}$ is a hydrogen atom, $C_{1-10}$alkyl, $C_{1-10}$alkoxy, $C_{3-10}$cycloalkyloxy, aryloxy, $C_{3-10}$cycloalkyl, aryl heteroaryl, —$C(=O)R^{30}$, or —$SiR^{23}R^{24}R^{25}$;

$R^{27}$ is hydroxy, $C_{1-10}$alkyl, $C_{3-10}$cycloalkyl, aryl, heteroaryl, —$SiR^{23}R^{24}R^{25}$, or —$C(=O)R^{30}$;

$R^{31}$ is a hydrogen atom, $C_{1-10}$alkyl, or $C_{3-10}$cycloalkyl;

$R^{32}$ is a hydrogen atom, $C_{1-10}$alkyl, $C_{3-10}$cycloalkyl, aryl, heteroaryl, —$SiR^{23}R^{24}R^{25}$, or —$C(=O)R^{30}$;

$R^{35}$ is a hydrogen atom, $C_{1-10}$alkyl, $C_{3-10}$cycloalkyl, $C_{2-10}$alkenyl, $C_{3-10}$cycloalkenyl, $C_{2-10}$alkynyl, $C_{1-10}$alkylthio, aryl, or heteroaryl;

$R^{36}$ is a hydrogen atom, $C_{1-10}$alkyl, $C_{3-10}$cycloalkyl, $C_{2-10}$alkenyl, $C_{3-10}$cycloalkenyl, or $C_{2-10}$alkynyl;

$R^{37}$ is a hydrogen atom, $C_{1-10}$alkyl, $C_{3-10}$cycloalkyl, $C_{2-10}$alkenyl, $C_{3-10}$cycloalkenyl, aryl, heteroaryl, —$SiR^{12}R^{13}R^{14}$, or —$C(=O)R^{15}$; and $R^{38}$ is $C_{1-10}$alkyl, $C_{3-10}$cycloalkyl, $C_{2-10}$alkenyl, $C_{3-10}$cycloalkenyl, $C_{2-10}$alkynyl, $C_{1-10}$alkylthio, aryl, heteroaryl, —$SiR^{23}R^{24}R^{25}$, or —$C(=O)R^{30}$;

which comprises:

Step a): treating a compound of Formula (II):

[Formula 4]

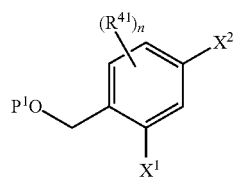

(II)

wherein $X^1$ and $X^2$ are independently selected from a bromine atom or an iodine atom;

$P^1$ is a metal ion, a hydrogen atom or a protecting group of hydroxy;

$R^{41}$ is a group defined as $R^1$, wherein the group may have one or more protecting groups; and n is as defined above;

with an organometal reagent, and then reacting with a compound of Formula (III):

[Formula 5]

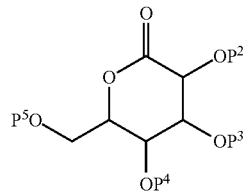

(III)

wherein $P^2$, $P^3$, $P^4$, and $P^5$ are independently selected from a protecting group of hydroxy; or $P^2$ and $P^3$, $P^3$ and $P^4$, and $P^4$ and $P^5$ together may independently represent a divalent group to protect two hydroxy groups and to form a ring; to obtain a compound represented by Formula (IVa):

[Formula 6]

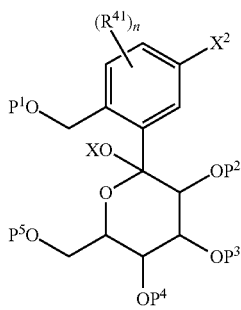

(IVa)

wherein $R^{41}$, n, $X^2$, $P^1$, $P^2$, $P^3$, $P^4$, and $P^5$ are as defined above; and X is a metal ion, or a hydrogen atom;

Step b): treating a compound represented by Formula (IVb):

[Formula 7]

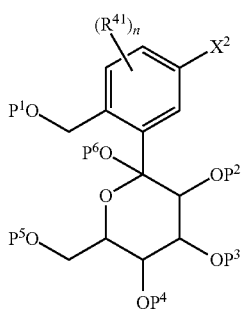

(IVb)

wherein $R^{41}$, n, $X^2$, $P^1$, $P^2$, $P^3$, $P^4$, and $P^5$ are as defined above; and $P^6$ is a metal ion, a hydrogen atom or a protecting group of hydroxy; with an organometal reagent, and then reacting with a compound represented by Formula (V):

[Formula 8]

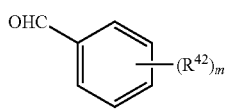

(V)

wherein $R^{42}$ is a group defined as $R^2$, wherein the group may have one or more protecting groups, and m is as defined above; and which may further comprise one or more steps to introduce a protecting group and/or to remove a protecting group, in the steps defined above, or in any stage prior to or after any one of the steps defined above.

In one embodiment on this aspect of the present invention, the process stated above further comprises:

Step c): subjecting a compound represented by Formula (VI):

[Formula 9]

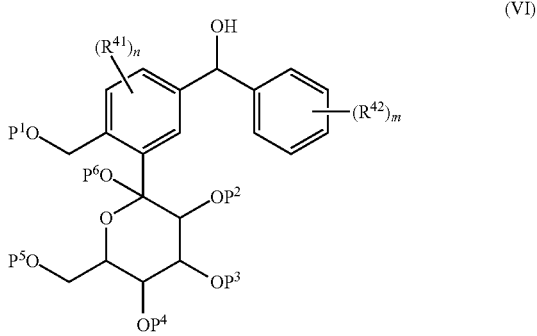

(VI)

wherein $R^{41}$, $R^{42}$, m, n, $P^1$, $P^2$, $P^2$, $P^4$, $P^5$, and $P^6$ are as defined above; to the two following steps:

Step (1): treating a compound represented by Formula (VI), wherein $P^1$ is a hydrogen atom, under acidic conditions, with the proviso that when $P^1$ is a protecting group, the step further comprises a deprotection step before the treatment; and Step (2): removing a hydroxy group, which is formed in Step b), by reduction reaction; with the proviso that any one of the two steps may be carried out in first; to obtain a compound represented by Formula (VII):

[Formula 10]

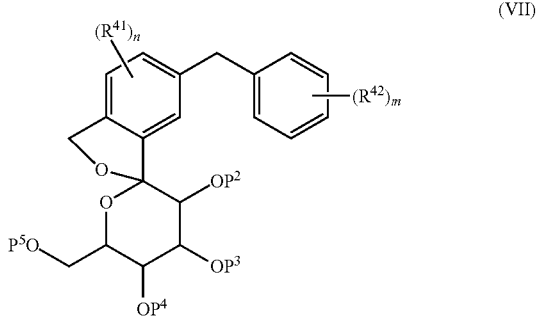

(VII)

wherein $R^{41}$, $R^{42}$, m, n, $P^2$, $P^3$, $P^4$, and $P^5$ are as defined above.

The term "a halogen atom" referred to herein means a fluorine atom, a chlorine atom, a bromine atom, an iodine atom and the like.

The term "$C_{1-10}$alkyl" means a linear or branched alkyl group having 1 to 10 carbon atoms. Examples include methyl, ethyl, n-propyl, i-propyl, n-butyl, s-butyl, I-butyl, t-butyl, n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3-ethylbutyl, 2-ethylbutyl, cyclopropylmethyl, cyclohexylmethyl and the like. $C_{1-10}$ alkyl further includes a linear or branched $C_{1-6}$alkyl and $C_{1-4}$alkyl.

The term "$C_{3-10}$cycloalkyl" means a cyclic alkyl group having 3 to 10 carbon atoms. Examples include cyclopropyl, cyclobutyl, cyclopentyl, cyclohexyl, cycloheptyl, cyclooctyl, methylcyclopropyl and the like. $C_{3-10}$cycloalkyl further includes $C_{3-8}$cycloalkyl and $C_{3-7}$cycloalkyl.

The term "$C_{2-10}$alkenyl" means a linear or branched alkenyl group having 2 to 10 carbon atoms. Examples include ethenyl (vinyl), 1-propenyl, 2-propenyl (allyl), propen-2-yl, 3-butenyl (homoallyl), 1,4-pentadien-3-yl and the like. $C_{2-10}$alkenyl further includes a linear or branched $C_{2-6}$alkenyl and $C_{2-4}$alkenyl.

The term "$C_{3-10}$cycloalkenyl" means a cyclic alkenyl group having 3 to 10 carbon atoms. Examples include cyclopentenyl, cyclohexenyl and the like. $C_{3-10}$cycloalkenyl further includes $C_{5-10}$cycloalkenyl and the like.

The term "$C_{2-10}$alkynyl" means a linear or branched alkynyl group having 2 to 10 carbon atoms. Examples include ethynyl, 1-propynyl, 2-propynyl and the like. $C_{2-10}$alkynyl further includes a linear or branched $C_{2-6}$alkynyl and $C_{2-4}$alkynyl.

The term "$C_{1-10}$alkoxy" means an alkyloxy group having a linear or branched alkyl group having 1 to 10 carbon atoms as an alkyl moiety. Examples include methoxy, ethoxy, n-propoxy, i-propoxy, n-butoxy, s-butoxy, i-butoxy, t-butoxy, n-pentoxy, 3-methylbutoxy, 2-methylbutoxy, 1-methylbutoxy, 1-ethylpropoxy, n-hexyloxy, 4-methylpentoxy, 3-methylpentoxy, 2-methylpentoxy, 1-methylpentoxy, 3-ethylbutoxy, 2-ethylbutoxy and the like. $C_{1-10}$alkoxy further includes a linear or branched $C_{1-6}$alkoxy and $C_{1-4}$alkoxy.

The term "$C_{1-10}$alkylamino" means an alkylamino group having a linear or branched alkyl group having 1 to 10 carbon atoms as an alkyl moiety. Examples include methylamino, ethylamino, n-propylamino, i-propylamino, n-butylamino, s-butylamino, i-butylamino, t-butylamino and the like. $C_{1-10}$alkylamino further includes a linear or branched $C_{1-6}$alkylamino and $C_{1-4}$alkylamino.

The term "di($C_{1-10}$alkyl)amino" means a dialkylamino group having linear or branched alkyl groups each having 1 to 10 carbon atoms as two alkyl moieties. The two alkyl moieties may be the same or different. Examples include dimethylamino, diethylamino, di(n-propyl)amino, di(i-propyl)amino, di(n-butyl)amino, di(s-butyl)amino, di(i-butyl)amino, di(t-butyl)amino, ethyl(methyl)amino, methyl(n-propyl)amino, methyl(i-propyl)amino, n-butyl(methyl)amino, s-butyl(methyl)amino, I-butyl(methyl)amino, t-butyl(methyl)amino and the like. Di($C_{1-10}$alkyl)amino further includes a linear or branched di($C_{1-6}$alkyl)amino and di($C_{1-4}$alkyl)amino.

The term "$C_{1-10}$alkylthio" means an alkylthio group having a linear or branched alkyl group having 1 to 10 carbon atoms as an alkyl moiety. Examples include methylthio, ethylthio, n-propylthio, i-propylthio, n-butylthio, s-butylthio, i-butylthio, t-butylthio and the like. $C_{1-10}$alkylthio further includes a linear or branched $C_{1-6}$alkylthio and $C_{1-4}$alkylthio.

The term "saturated, partially unsaturated or unsaturated heterocyclyl" referred to herein means for example saturated, partially unsaturated or unsaturated 4- to 10-membered heterocyclic group containing one or more heteroatoms selected from a nitrogen atom, an oxygen atom and a sulfur atom. Examples of the heterocyclyl include pyridyl, pyrimidinyl, pyrazinyl, triazinyl, quinolyl, quinoxalinyl, quinazolinyl, furyl, thienyl, pyrrolyl, pyrazolyl, imidazolyl, triazolyl, pyrrolidinyl, piperidyl, piperazinyl, homopiperidyl, homopiperazinyl, morpholinyl and the like.

The term "aryl" is not particularly limited, but means an aryl group having an aromatic hydrocarbon ring with 6 to 14 carbon atoms, for example 6 to 10 carbon atoms. Examples include phenyl, 1-naphthyl, 2-naphthyl and the like.

The term "heteroaryl" is not particularly limited, but means a 4- to 10-membered aromatic heterocyclic group containing one or more heteroatoms selected from a nitrogen atom, an oxygen atom and a sulfur atom. Examples of the heteroaryl include pyridyl, pyrazinyl, triazinyl, quinolyl, quinoxaling, quinazolinyl, furyl, thienyl, pyrrolyl, pyrazolyl, imidazolyl, triazolyl and the like.

The term "a carbocyclic ring" referred to herein is not particularly limited, but means a hydrocarbon ring having 6 to 14 carbon atoms, for example 6 to 10 carbon atoms. Examples include benzene, naphthalene and the like.

The term "a heterocyclic ring" referred to herein is not particularly limited, but means a 4- to 10-membered heterocyclic ring containing one or more heteroatoms selected from a nitrogen atom, an oxygen atom and a sulfur atom. Examples of the heterocyclic ring include pyridine, pyrimidine, pyrazine, triazine, quinoline, quinoxaline, quinazoline, furan, thiophene, pyrrole, pyrazole, imidazole, triazole and the like.

In the present invention, when the group defined as $R^1$ and $R^2$ has one or more protectable groups such as hydroxy, carboxy, carbonyl, amino, and mercapto, the group may be protected by a protecting group. Selection of a protecting group introduced to each group and operations for introduction and removal of a protecting group can be carried out, for example, as described in Greene and Wuts, "Protective Groups in Organic Synthesis," (4th edition, John Wiley & Sons, 2006).

Examples of a protecting group for a hydroxy group, which may be contained in $R^1$ and/or $R^2$, include $C_{1-10}$alkyl optionally substituted with one or more $R^{51}$, saturated, partially unsaturated or unsaturated heterocyclyl optionally substituted with one or more $R^{52}$, $C_{2-10}$alkenyl, —Si$(R^{53})_3$, —C(=O)$R^{54}$, —B(O$R^{55}$)$_2$ and the like;
  wherein $R^{51}$ is independently selected from aryl optionally substituted with one or more $R^{56}$, $C_{1-10}$alkoxy optionally substituted with one or more aryl, $C_{1-10}$alkylthio, and arylselenyl;
  $R^{52}$ is independently selected from $C_{1-10}$alkoxy;
  $R^{53}$ and $R^{55}$ are independently selected from $C_{1-10}$alkyl and aryl;
  $R^{54}$ is a hydrogen atom, $C_{1-10}$alkyl, aryl optionally substituted with one or more $C_{1-10}$alkoxy, heteroaryl, amino optionally substituted with one or more $R^{57}$, $C_{1-10}$alkoxy optionally substituted with one or more aryl, or aryloxy optionally substituted with one or more nitro;
  $R^{56}$ is independently selected from $C_{1-10}$alkyl, $C_{1-10}$alkoxy, aryl, and heteroaryl;
  $R^{57}$ is independently selected from $C_{1-10}$alkyl and aryl.

Preferred examples of a protecting group of hydroxy include methyl, benzyl, methoxymethyl, methylthiomethyl, 2-methoxyethoxymethyl, benzyloxymethyl, tetrahydropyranyl, tetrahydrothiopTanyl, tetrahydrofuranyl, tetrahydrothiophenyl, 1-ethoxyethyl, 1-methoxy-1-methylethyl, t-butyl, allyl, vinyl, triphenylmethyl (trityl), trimethylsilyl, triethylsilyl, t-butyldimethylsilyl, isopropyldimethylsilyl, t-butyldiphertylsilyl, isobutyryl, pivaloyl, benzoyl, methoxycarbonyl, ethoxycarbonyl, isopropoxycarbonyl, benzyloxycarbonyl, t-butoxycarbonyl, and the like.

Examples of a protecting group for an amino group, which may be contained in $R^1$ and/or $R^2$, include $C_{1-10}$alkyl optionally substituted with one or more $R^{51}$, saturated, partially unsaturated or unsaturated heterocyclyl optionally substituted with one or more $R^{52}$, $C_{2-10}$alkenyl, —Si$(R^{53})_3$, —C(=O)$R^{54}$, and the like; wherein $R^{51}$, $R^{52}$, $R^{53}$, and $R^{54}$ are as defined hereinbefore. Preferred examples of a protective group of amino group include benzyl. Further, a primary amino group can be protected by converting it to a phthalimido group or a succinimido group.

Examples of a protecting group for a carboxy group, which may be contained in $R^1$ and/or $R^2$, include an ester-forming group such as $C_{1-10}$alkyl optionally substituted with one or more $R^{51}$, $C_{2-10}$alkenyl, —Si$(R^{53})_3$, wherein $R^{51}$ and $R^{53}$ are as defined hereinbefore; and an amide-forming group such as —NR$^{58}$R$^{59}$, wherein $R^{58}$ and $R^{59}$ are independently selected from $C_{1-10}$alkyl optionally substituted with one or more $R^{51}$, $C_{2-10}$alkenyl, and —Si$(R^{53})_3$, and $R^{51}$ and $R^{53}$ are as defined hereinbefore. Preferred examples of conversion by introducing a protective group to carboxy include ethyl ester, benzyl ester, and t-butyl ester.

The group formed by introducing one or more protecting groups into the group defined as $R^1$ and $R^2$ is included within the definitions of $R^{41}$ and $R^{42}$.

$R^1$ and $R^2$ defined in the present invention are not limited particularly, but are independently selected from, for example, $C_{1-10}$alkyl optionally substituted with one or more Ra, $C_{3-10}$cycloalkyl optionally substituted with one or more Ra, $C_{2-10}$alkenyl optionally substituted with one or more Ra, $C_{3-10}$cycloalkenyl optionally substituted with one or more Ra, $C_{2-10}$alkynyl optionally substituted with one or more Ra, aryl optionally substituted with one or more Ra, saturated, partially unsaturated or unsaturated heterocyclyl optionally substituted with one or more Ra, and —SiR$^{12}$R$^{13}$R$^{14}$. More preferably $R^1$ and $R^2$ are independently selected from $C_{1-6}$alkyl, $C_{3-6}$cycloalkyl, aryl and —SiR$^{12}$R$^{13}$R$^{14}$. In the present invention, when n or m is 0, $R^1$ or $R^2$ does not exist respectively on the benzene ring. In one embodiment of the present invention, n is 0, m is 0 or 1, and $R^2$ is $C_{1-4}$alkyl.

The halogen atom defined as $R^1$ and $R^2$ is preferably a fluorine atom or a chlorine atom.

The metal ion defined in $P^1$, $P^6$ and X means a metal ion, which can be a counter ion of an alkoxide ion. Examples thereof include an alkali metal ion and an alkaline earth metal ion such as a lithium ion, a sodium ion, a potassium ion, a cesium ion, and a magnesium ion. The metal ion may form a complex with other metal. Examples of the metal ion also include a metal ion formed by reacting an organometal reagent used in the present invention with a hydroxy group (e.g. a lithium ion).

A protecting group of hydroxy included in the definitions of $P^1$ to $P^6$ is not limited as long as it is commonly used as a protecting group of hydroxy. A protecting group can be selected and introduced to a hydroxy group in line with the description in Greene and Wuts, "Protective Groups in Organic Synthesis" (4th edition, John Wiley & Sons, 2006). Examples thereof include $C_{1-10}$alkyl optionally substituted with one or more $R^{51}$, saturated, partially unsaturated or unsaturated heterocyclyl optionally substituted with one or more $R^{52}$, $C_{2-10}$alkenyl, —Si$(R^{53})_3$, —C(=O)R$^{54}$, —B(OR$^{55})_2$ and the like.

The term "a divalent group to protect two hydroxy groups and to form a ring" referred to herein means a divalent group linking two oxygen atoms of two hydroxy groups such as $C_{1-10}$alkylene group (for example, methylene, methylmethylene, dimethylmethylene), carbonyl group and the like.

An organometal reagent used in the present invention is not limited as long as it is suitable for a halogen-metal exchange reaction on a benzene ring. Examples include $C_{1-10}$alkyllithium (for example, n-butyllithium, s-butyllithium, t-butyllithium), aryllithium (for example, phenyllithium, naphthyllithium, dimethoxyphenyllithium), $C_{1-10}$alkylmagnesium halide (for example, n-butylmagnesium chloride, isopropylmagnesium chloride), di($C_{1-10}$alkyl) magnesium (for example, di(n-butyl) magnesium) and the like. The organometal reagent may be used in the presence of an inorganic salt or an organic salt (for example, lithium chloride, lithium bromide, lithium iodide, lithium fluoride, lithium triflate, magnesium chloride, magnesium bromide, magnesium triflate), or may be used as a mixture with the inorganic salt or the organic salt. Examples of the organometal reagent also include, for example, a mixture or reaction product of magnesium compounds and organolithium compounds described in pages 11 to 17 of WO 2001/057046; a mixture or a reaction product of butylmagnesium chloride and butyllithium; isopropylmagnesium bromide and butyllithium; isopropylmagnesium bromide and lithium chloride; dibutylmagnesium and butyllithium; dibutylmagnesium and ethoxylithium; dibutylmagnesium and t-butoxylithium; dibutylmagnesium and lithium hexamethyldisilazide; butylmagnesium bromide and butyllithium; isopropylmagnesium bromide, butyllithium and lithium chloride; butylmagnesium chloride, butyllithium and ethoxylithium; butylmagnesium chloride, butyllithium and lithium hexamethyldisilazide; isopropylmagnesium bromide, butyllithium and ethoxylithium; zinc chloride and butyllithium, diethylzinc and butyllithium; and organozinc complex described in JP 2004-292328 A.

For example, in Steps a) and b), n-butyllithium is used as an organometal reagent. Also, a metal complex formed by sequentially reacting two or more organometal reagents may be used as an organometal reagent. For example, after treating a compound represented by Formula (II) with butyllithium, butylmagnesium chloride and butyllithium may be added to the reaction system followed by reaction with a compound represented by Formula (III).

A substituted silyl group defined herein by the formulae —SiR$^{12}$R$^{13}$R$^{14}$, —SiR$^{23}$R$^{24}$R$^{25}$, —Si$(R^{53})_3$ and the like is not particularly limited. Examples thereof include trimethylsilyl, triethylsilyl, t-butyldimethylsilyl, isopropyldimethylsilyl, t-butyldiphenyisilyl and the like.

In a compound represented by Formula (II) used in Step a), both $X^1$ and $X^2$ are, for example, a bromine atom. Examples of $P^1$ include a lithium ion, a hydrogen atom, and a protecting group such as $C_{1-6}$alkoxy$C_{1-6}$alkyl (for example, methoxymethyl, ethoxymethyl, 1-methoxyethyl, 1-methoxy-1-methylethyl), arylmethyloxy$C_{1-6}$alkyl (for example, benzyloxymethyl), tetrahydropyranyl, a group —Si$(R^{53})_3$ (for example, trimethylsilyl, t-butyldimethylsilyl, isopropyldimethylsilyl, t-butyldiphenylsilyl), aralkyl(for example, benzyl, 4-methoxybenzyl, trityl), a group —B(OR$^{55})_2$ and the like.

In Step a), the treatment of a compound represented by Formula (II) with an organometal reagent may be carried out in an solvent, which is suitable for a halogen-metal exchange reaction. Examples of the solvent include ethers (for example, tetrahydrofuran (THF), methyltetrahydrofuran, diethyl ether, t-butylmethyl ether, diisopropyl ether, cyclopentylmethyl ether, 1,2-dimethoxyethane), hydrocarbons (for example, pentane, hexane, heptane, benzene, toluene), N,N-tetramethylethylenediamine, N,N-tetramethylpropanediamine, and a mixed solvent of two or more solvents indicated above. When $P^1$ is a metal ion or a protecting group, an organometal reagent may be used in an amount of 0.5 to 1.5 equivalents, for example, 0.8 to 1.1 equivalents. When $P^1$ is a hydrogen atom, an organometal reagent may be used in an amount of 1.5 to 3.0 equivalents, for example, 1.8 to 2.2 equivalents.

From the viewpoint of enhancing regioselectivity, an organometal reagent may be added in portions. For example, an organometal reagent may be added over 15 minutes or more, preferably over 15 to 300 minutes, more preferably over 30 to 300 minutes. Further, the reagent may be added intermittently, and the addition time stated above may include one or more interruptions. For example, an organometal reagent may be added in two or three portions with one or two interruptions, for example, each for 5 to 300 minutes, preferably for 15 to 120 minutes.

In addition, from the viewpoint of enhancing regioselectivity, after completion of addition of an orzanometal reagent, an aryl halide may be added to the reaction mixture in a certain amount, for example, 0.05 to 0.5 equivalents, preferably 0.1 to 0.4 equivalents, relative to the amount originally included in the reaction mixture. Examples of aryl halide include iodobenzene, diiodotoluene, dibromotoluene, the reaction substrate (for example, 2,4-dibromo-1-(1-methoxy-1-methylethoxymethyl)benzene) and the like. Preferably the reaction substrate may be used as an aryl halide.

From the viewpoint of enhancing regioselectivity, an organometal reagent may be added, for example, at a temperature of −80 to 30° C., preferably −60 to 25° C., particularly −15 to 0° C., in portions (for example, dropwise) to the reaction system. After addition of the reagent, the reaction mixture may be stirred at an appropriate temperature (for example, −80 to 0° C., preferably −15 to 0° C.) for a certain period of time (for example, 0.1 to 5 hours) to complete the reaction.

From the viewpoint of enhancing regioselectivity, when $P^1$ is a metal ion or a protecting group, an organometal reagent may be added in an amount of less than 1 equivalent, for example 0.4 to 0.9 equivalents, preferably 0.8 equivalents and then the reaction mixture may be stirred at an appropriate temperature, for example −80 to 30° C., preferably −60 to 25° C., particularly −15 to 0° C., for a certain period of time, for example 0.1 to 5 hours, preferably 0.5 to 2 hours. After then an organometal reagent may be further added in an amount of for example 0.1 to 0.7 equivalents, preferably 0.3 equivalents, and then the reaction mixture may be stirred at an temperature of, for example −80 to 30° C., preferably −60 to 25° C., particularly −15 to 0° C., for a certain period of time, for example, 0.1 to 5 hours, preferably 0.5 to 2 hours. The numbers of equivalent indicated above mean a molar equivalent relative to a compound represented by Formula (II) used as a reactive substrate. It should be noted that the term "equivalent" refers to "molar equivalent" in the specification, unless otherwise specified.

From the viewpoint of enhancing regioselectivity, when $P^1$ is a hydrogen atom, an organometal reagent may be added in an amount of less than 2 equivalents for example 1.4 to 1.9 equivalents, preferably 1.8 equivalents and then the reaction mixture may be stirred at an appropriate temperature, for example −80 to 30° C., preferably −60 to 25° C., particularly −15 to 0° C., for a certain period of time, for example 0.1 to 5 hours, preferably 0.5 to 2 hours. After then an organometal reagent may be further added in an amount of for example 0.1 to 0.7 equivalents, preferably 0.3 equivalents, and then the reaction mixture may be stirred at a temperature of, for example −80 to 30° C., preferably −60 to 25° C., particularly −15 to 0° C., for a certain period of time, for example, 0.1 to 5 hours, preferably 0.5 to 2 hours. The numbers of equivalent indicated above mean a molar equivalent relative to a compound represented by Formula (II) used as a reactive substrate.

In the reaction of Step a), a halogen-metal exchange reaction preferentially occurs at $X^1$ of the compound of Formula (II), which has plural reactive sites in the molecule, and accordingly the reaction provides more amount of the desired compound of Formula (IVa) than that of a by-product that is provided by a halogen-metal exchange reaction at $X^2$. In this regard, the reaction in Step a) is a regioselective reaction. The regioselectivity of the reaction in Step a) is not limited particularly. However, the ratio of the desired compound: the by-product in the reaction of Step a) is, for example, 10:1 or more, preferably 30:1 or more.

After a halogen-metal exchange reaction by using $C_{1-10}$alkyllithium (for example, n-butyllithium, s-butyllithium, or t-butyllithium), aryllithium (for example, phenyllithium, naphthyllithium, dimethoxyphenyllithium), another organometal reagent (for example, n-butylmagnesium chloride and n-butyllithium, or dibutylmagnesium) may be added thereto, and then the reaction mixture may be stirred at an appropriate temperature of for example, −80 to 30° C., preferably −60 to 25° C., particularly −15 to 0° C., for a certain period of time, for example, 0.1 to 5 hours, preferably 0.5 to 2 hours to form a complex.

In one embodiment of the present invention, a compound represented by Formula (II) wherein $P^1$ is a hydrogen atom is used in Step a).

In a compound represented by Formula (III) used in Step a), examples of $P^2$, $P^3$, $P^4$, and $P^5$ include a protecting group such as $C_{1-6}$alkoxy$C_{1-6}$alkyl (for example, methoxymethyl, ethoxymethyl, 1-methoxyethyl, 1-methoxy-1-methylethyl), arylmethyloxy$C_{1-6}$alkyl (for example, benzyloxymethyl), tetrahydropyranyl, a group:
—Si($R^{53}$)$_3$ (for example, trimethylsilyl, t-butyldimethylsilyl, isopropyldimethylsilyl, t-butyldiphenylsilyl), aralkyl (for example, benzyl, 4-methoxybenzyl, triphenylmethyl), a group: —B(O$R^{55}$)$_2$, $C_{1-6}$alkylcarbonyl (for example, acetyl, propionyl, pivaloyl), $C_{1-6}$alkoxycarbonyl (for example, methoxycarbonyl, isopropyloxycarbonyl, t-butoxycarbonyl, benzyloxycarbonyl), t-butyl. Further, $P^4$ and $P^5$ together may represent a divalent group to protect two hydroxy groups and to form a ring (for example, —CH$_2$—, —CH(CH$_3$)—, —C(CH$_3$)$_2$—, —CHPH—).

A reaction of a compound of Formula (II), which is treated with an organometal reagent, with a compound of Formula (III) may be carried out, for example by adding a solution of a compound of Formula (II) in an appropriate solvent in portions (for example, dropwise) to a reaction mixture containing a compound of Formula (III) (for example, 1.0 to 1.1 equivalents) at an appropriate temperature of, for example, —100 to 0° C., preferably −90 to −30° C., particularly −80 to −40° C. Examples of an appropriate solvent include ethers (for example, tetrahydrofuran (THF), methyltetrahydrofuran, diethyl ether, t-butylmethyl ether, diisopropyl ether, cyclopentylmethyl ether, 1,2-diinethoxyethane), hydrocarbons (for example, hexane, heptane, benzene, toluene) and the like, and a mixture of two or more solvents stated above. After addition of a compound of Formula (II), the reaction may be completed by stirring for a certain period of time (for example, 0.5 to 5 hours), at an appropriate temperature of for example, −80 to −40° C.

A conventional procedure may be used for workup of the reaction. The resulting product may be purified by a conventional procedure to give a compound of Formula (IVa). From the viewpoint of simplification of production processes, reduction in the amount of solvents used and production costs, it is preferred that the next step is carried out without workup procedure of this reaction.

The process of the present invention may include a step for introducing a protecting group to a compound of Formula (IVa) to obtain a compound of Formula (IVb) wherein $P^6$ is a protecting group of hydroxy. Introduction of a protecting group in the step may be carried out, for example, after addition of a compound of Formula (II) previously treated with an organometal reagent to a compound of Formula (III), a reagent for introducing a protecting group (for example, 1.0 to 2.0 equivalents) is added to the reaction mixture, if necessary together with an appropriate amount (for example, 0.1 to 1.0 equivalent) of a base, for example, triethylamine, N-methylmorpholine, ethyldiisopropylamine and the like, at an appropriate temperature of for example, −100 to 0° C., preferably −90-60° C., particularly 80 to −75° C. After addition of the reagent, the reaction may be completed by stirring for a certain period of time (for example, 0.1 to 5 hours) at the same or elevated temperature.

Examples of a reagent for introducing a protecting group include a silylation reagent such as trimethylsilyl chloride, triethylsilyl chloride, t-butyldimethylsilyl chloride, isopropyldimethylsilyl chloride, and t-butyldiphenylsilyl chloride; an alkylhalide such as methyl iodide, and benzyl bromide; an acid halide such as pivaloyl chloride; a $C_{1-6}$alkoxy$C_{1-6}$alkyl halide such as methoxymethyl chloride, and ethoxymethyl chloride; and the like. When $P^1$ of a compound of Formula (IVa) is a metal ion or a hydrogen atom, a protecting group may be introduced to the site to obtain a compound of Formula (IVb) wherein $P^1$ is a protecting group of hydroxy by using an appropriate amount of the reagent in this step. Accordingly, in one embodiment of the present invention, a compound of Formula (IVb) wherein $P^6$ is a protecting group of hydroxy is used in Step b).

A conventional procedure may be used for workup of the reaction for introducing a protecting group. The resulting product may be purified by a conventional procedure to give a compound of Formula (IVb). From the viewpoint of simplification of production processes, reduction in the amount of solvents used and production costs, it is also preferred that the next step is carried out without workup procedure of this reaction.

Treatment of a compound of Formula (IVb) with an organometal reagent in Step b) may be carried out by using a solvent suitable for a halogen-metal exchange reaction. Examples of the solvent include ethers (for example, tetrahydrofuran (THF), methyltetrahydrofuran, diethyl ether, t-butylmethyl ether, diisopropyl ether, cyclopentylmethyl ether, 1,2-dimethoxyethane), hydrocarbons (for example, pentane, hexane, heptane, benzene, toluene) and the like, and a mixture of two or more solvents stated above. When workup procedure is not carried out in the previous step, a solvent used in the previous step may be used.

An organometal reagent may be used in an amount of 0.3 to 4.0 equivalents, for example, 1.0 to 3.0 equivalents, preferably 1.1 to 2.1 equivalents.

The organometal reagent may be added to the reaction system in portions (for example, dropwise) at an temperature of, for example, −100 to 30° C., preferably −90 to −10° C., particularly −90 to −70° C. After addition of an organometal reagent, the reaction may be stirred for a certain period of time of, for example, 0.1 to 5 hours, preferably 0.5 to 2 hours at an appropriate temperature of, for example, −100 to 30° C., preferably −90 to −10° C., particularly −90 to −70° C., A reaction of a compound of Formula (IVb), which is treated with an organometal reagent, with a compound of Formula (V) may be carried out, for example, by adding a solution of a compound of Formula (V) in an appropriate solvent, at an appropriate temperature of, for example, −100 to 30° C., preferably −90 to −10° C., particularly −80 to −70° C., to a reaction mixture containing a compound of Formula (IVb). In this regard, a compound of Formula (V) may be used in an amount of 1.0 to 15.0 equivalents, for example, 1.0 to 5.0 equivalents, preferably 1.1 to 2.2 equivalents. Examples of an appropriate solvent include, for example, ethers (for example, tetrahydrofuran (THF), methyltetrahydrofuran, diethyl ether, t-butylmethyl ether, diisopropyl ether, cyclopentylmethyl ether, 1,2-dimethoxyethane), hydrocarbons (for example, pentane, hexane, heptane, benzene, toluene) and the like, and a mixture of two or more solvents stated above. After addition of Formula (V), the reaction may be completed by stirring for a certain period of time of, for example, 0.1 to 5 hours at an appropriate temperature of for example, −90 to 0° C.

A conventional procedure may be used in workup of the reaction in Step b). The resulting product may be purified by a conventional procedure to obtain a compound of Formula (VI). From the viewpoint of simplification of production processes, reduction in the amount of solvents used and production costs, it is preferred that the next step is carried out without workup procedure of this reaction.

A compound of Formula (VI) wherein $P^1$ is a protecting group of hydroxy is converted to a compound wherein $P^1$ is a hydrogen atom by carrying out deprotection prior to Step (1) in Step c). In one embodiment of the present invention, protecting groups introduced as $P^2$ to $P^6$ are also removed by the deprotection. Deprotection may be carried out by a procedure well known in the art pertaining to the present invention, for example, by using an acid or a Lewis acid such as hydrochloric acid, sulfuric acid, acetic acid, trifluoroacetic acid, p-toluenesulfonic acid, boron trifluoride diethyl ether complex, boron trichloride, and boron tribromide; a base such as sodium hydroxide, lithium hydroxide, potassium hydroxide, and potassium carbonate; an organometal reagent such as butyllithium, and Grignard reagent; a metal hydride reagent such as lithium aluminum hydride, lithium borohydride, and diisobutylaluminum hydride; a combination reagent of a Lewis acid and a nucleophile such as boron trifluoride diethyl ether complex and ethanethiol, aluminum halide and sodium iodide, aluminum halide and a thiol, and aluminum halide and a sulfide; or by hydrogenation using a catalyst such as palladium on carbon, platinum, a homogeneous palladium complex, a homogeneous ruthenium complex, and a homogeneous rhodium complex.

A spiro ring structure is formed by treatment in Step (1). The reaction in Step (1) may be carried out in an appropriate solvent such as tetrahydrofuran (THF), methyltetrahydrofuran, 1,2-dimethoxyethane, acetonitrile, dimethyl sulfoxide, N,N-dimethylformamide, N,N-dimethylacetamide, N-methylpyrrolidone, acetone, acetic acid ester (for example, ethyl acetate, methyl acetate, isopropyl acetate and the like), methylene chloride, chloroform, dichloroethane, water, or a mixture of two or more solvents stated above at an appropriate temperature of, for example, −20 to 100° C., preferably 0 to 80° C., particularly 20 to 30° C. The reaction time may be set appropriately, for example, for about 0.5 to 15 hours, preferably for about 2 to 10 hours. An acid used is not particularly limited, but a Lewis acid may be used. Specific examples thereof include hydrochloric acid, sulfuric acid, acetic acid, trifluoroacetic acid, p-toluenesulfonic acid, boron trifluoride diethyl ether complex, boron trichloride, and boron tribromide.

In one embodiment of the present invention, removal of protecting groups introduced as $P^1$ to $P^6$ and formation of a spire ring can be carried out at the same time by treatment under acidic conditions in Step (1).

A reduction reaction in Step (2) of Step c) may be carried out in an appropriate solvent such as tetrahydrofuran (THF), methyltetrahydrofuran, 1,2-dimethoxyethane, methanol, ethanol, isopropanol, acetic acid ester (for example, ethyl acetate, methyl acetate, isopropyl acetate), acetone, water, or a mixture of two or more solvents stated above at an appropriate temperature of, for example, −80 to 80° C., preferably −30 to 70° C., particularly −20 to 60° C. The reaction time may be set appropriately, for example, for 0.5 to 24 hours, preferably about 5 to 15 hours. The reduction reaction is not limited particularly, but the reaction may be carried out by using a reduction reagent and/or a catalyst suitable for removing a hydroxy group on a carbon atom that links two benzene rings in a compound of Formula (VI). Examples of a reduction reagent and a catalyst include a metal catalyst under a hydrogen atmosphere (for example, palladium on carbon, platinum, a homogeneous palladium complex, a homogeneous ruthenium complex, a homogeneous rhodium complex); a hydride reduction reagent in combination with a Lewis acid (for example, aluminum chloride and sodium borohydride, trifluroacetic acid and triethylsilane).

In one embodiment of the present invention, removal of a protecting group(s) introduced as $P^1$ to $P^6$ and removal of the hydroxy group may be carried out simultaneously by the reduction reaction in Step (2). Either Step (1) or (2) in Step c) may be carried out first. Deprotection of $P^1$ or $P^1$ to $P^6$ may be carried out in any stage prior to Step (1).

The process of the present invention may further comprise a step for removing any protecting group included in a compound obtained in Step c). The process may also comprise a step for converting a compound of Formula (I) obtained by the process of the present invention to another compound of Formula (I).

In one embodiment of the present invention, Steps a) and b) may be carried out in a one-pot reaction. Namely, the steps may be carried out by adding necessary reagents in order without operating any workup procedures or purifications. Therefore, the process of the present invention is advantageous in that the process can be carried out in a one-pot reaction to achieve simplification of production steps, reduction in the amount of solvents used and production costs, as well as in that a desired compound can be obtained in excellent yield.

According to another aspect of the present invention, there is provided a process for preparing a high-purity compound represented by Formula (I) defined hereinbefore, which comprises:

Step d): converting a compound of Formula (I) to a compound of Formula (X):

[Formula 11]

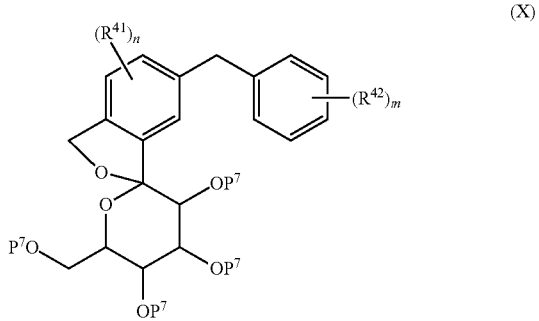

(X)

wherein $R^{41}$, $R^{42}$, m, and n are as defined hereinbefore, and $P^7$ is a protecting group of hydroxy;

Step e): crystallizing the compound of Formula (X) and purifying the compound by recrystallization;

Step f): removing a protecting group(s) from a o pound of Formula (X) to give a high-purity compound of Formula (I).

Examples of a compound of Formula (X) indicated above include compounds of Formulae (Xa) and (Xb):

[Formula 12]

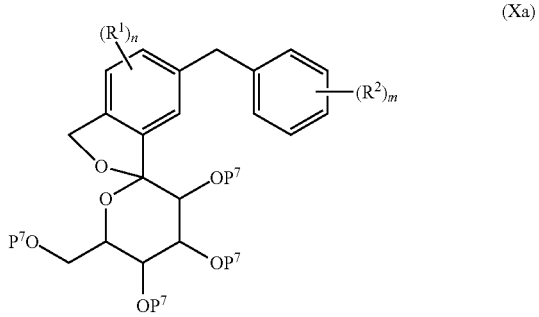

(Xa)

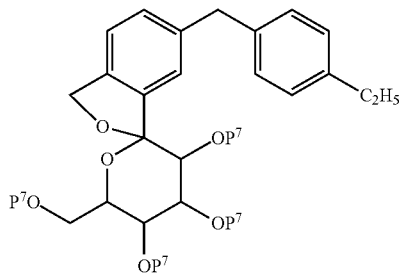

(Xb)

A protecting group of hydroxy defined as $P^7$ is not limited particularly as long as it is commonly used for protecting a hydroxy group. Examples thereof include protecting groups described in Greene and Wuts, "Protective Groups in Organic Synthesis" (the forth edition, John Wiley & Sons 2006). Examples of a protecting group of hydroxy also include $C_{1-10}$alkyl optionally substituted with one or more $R^{51}$, saturated, partially unsaturated or unsaturated heterocyclyl optionally substituted with one or more $R^{52}$, $C_{2-10}$alkenyl, —Si$(R^{53})_3$, —C(=O)$R^{54}$, —B(O$R^{55})_2$, wherein $R^{51}$ to $R^{55}$ are as defined above.

In one embodiment of the present invention, $P^7$ is selected from $C_{1-6}$alkylcarbonyl, $C_{1-6}$alkoxycarbonyl, and —Si$R^{23}R^{24}R^{25}$, wherein $R^{23}$, $R^{24}$, and $R^{25}$ as defined above.

A reaction for introducing a protecting group in Step d) may be carried out in a manner well known in the art pertaining to the present invention. For example, a reagent and a reaction condition described in Greene and Wuts, "Protective Groups in Organic Synthesis" (the forth edition, John Wiley & Sons 2006) may be used in the reaction. Examples of a solvent used in the reaction include ethers (for example, tetrahydrofuran (THF), methyltetrahydrofuran, diethyl ether, t-butylmethyl ether, diisopropyl ether, cyclopentylmethyl ether, 1,2,-dimethoxyethane), hydrocarbons (for example, benzene, toluene), acetonitrile. N,N-dimethylformamide, N,N-dimethylacetamide, N-methylpyrrolidone, acetone, acetic acid ester (for example, ethyl acetate, methyl acetate, isopropyl acetate), methylene chloride, chloroform, dichloroethane, water, and a mixture of two or more solvents stated above.

A reagent used for introducing a protecting group can be selected based on a protecting group to be introduced. For example, $C_{1-6}$alkylcarbonyl chloride, $C_{1-6}$alkoxycarbonyl chloride, Cl—Si$R^{23}R^{24}R^{25}$ and the like may be used in an amount of 1.0 to 4.0 equivalents, preferably 1.0 to 3.0 equivalents relative to a hydroxy group. If necessary, a base may be used. Examples of the base include triethylamine, pyridine, N,N-dimethylaniline, 4-(dimethylamino)pyridine, imidazole, 1-methylimidazole, ethyldiisopropylamine, lutidine, morpholine, potassium carbonate, sodium carbonate, and sodium hydrogen carbonate. Preferably 1-methylimidazole may be used. A reaction temperature is not limited particularly, but the reaction may be carried out at a temperature of for example, −20 to 50° C., preferably −10 to 25° C., for a certain period of time of, for example, 1 to 10 hours, preferably 2 to 4 hours.

Crystallization in Step e) may be carried out by using an appropriate solvent such as methanol, ethanol, propanol, isopropanol, butanol, ethylene glycol ethyl acetate, isopropyl acetate, tetrahydrofuran, t-butylmethyl ether, cyclopentylmethyl ether, 1,2-dimethoxyethane, diisopropyl ether, acetonitrile, acetone, dimethyl sulfoxide, N,N-dimethylformamide, N,N-dimethylacetamide, N-methylpyrrolidone, heptane, toluene, or water, or a mixture of two or more solvents stated above. Also recrystallization in the step may be carried out in a manner well known in the art pertaining to the present invention by using an appropriate solvent such as methanol, ethanol, propanol, isopropanol, butanol, ethylene glycol, ethyl acetate, isopropyl acetate, tetrahydrofuran, t-butylmethyl ether, cyclopentylmethyl ether, 1,2-dimethoxyethane, diisopropyl ether, acetonitrile, acetone, dimethyl sulfoxide, N,N-dimethylformamide, N,N-dimethylacetamide, N-methylpyrrolidone, heptane, toluene, or water, or a mixture of two or more solvents stated above.

Deprotection may be carried out by selecting a method known in the art pertaining to the present invention, which is suitable for the protecting group to be removed. For example, a reagent and a reaction condition described in Greene and Wuts, "Protective Groups in Organic Synthesis" (the forth edition, John Wiley & Sons 2006) may be used. For example, deprotection may be carried out by using an acid or a Lewis acid such as hydrochloric acid, sulfuric acid, acetic acid, trifluoroacetic acid, p-toluenesulfonic acid, boron trifluoride diethyl ether complex, boron trichloride, and boron tribromide; a base such as sodium hydroxide, lithium hydroxide, potassium hydroxide, and potassium carbonate; an organometal reagent such as butyllithium, and Grignard reagent; a metal hydride reagent such as lithium aluminum hydride, lithium borohydride, and diisobutylaluminum hydride; a combination reagent of a Lewis acid and a nucleophile such as boron trifluoride diethyl ether complex and ethanethiol, aluminum halide and sodium iodide, aluminum halide and a thiol, and aluminum halide and a sulfide; or by hydrogenation using a catalyst such as palladium on carbon, platinum, a homogeneous palladium complex, a homogeneous ruthenium complex, and a homogeneous rhodium complex and the like.

In one embodiment of the present invention, a crude product obtained in a process comprising Steps to c) defined herein is used as a compound of Formula (I) in Step d). In a process comprising Steps a) to c) defined hereinbefore, a desired product can be produced without purification. Therefore, from the viewpoint of enhancing production efficiency, it is advantageous to combine the process comprising Steps a) to c) with Steps d) to f) in which high purification can be carried out. Also, Steps d) to f) may be combined with another process for preparing a compound of Formula (I).

In the present invention, the term "high-purity" means improved purity compared with a compound of Formula (I) used as a starting material of Step d). Examples of a high-purity compound of Formula (I) include a compound of Formula (I) having purity of 90.0% by weight or more, preferably 97.0% by weight or more.

In one embodiment of the present invention, the process of the invention further comprises a step for crystallizing a high-purity compound of Formula (I) obtained in Step f). A solvent used for crystallization is for example a solvent selected from water; alcohols such as methanol, ethanol, propanol, isopropanol, butanol, ethylene glycol, and 1-hexanol; ethers such as tetrahydrofuran, t-butylmethyl ether, cyclopentylmethyl ether, 1,2-dimethoxyethane, and diisopropyl ether; esters such as ethyl acetate, propyl acetate, and hexyl acetate; amides such as N,N-dimethylformamide, N,N-dimethylacetamide, N-methylpyrrolidone, and N,N-dibutylformamide; halogenated hydrocarbons such as I-chlorohexane; hydrocarbons such as n-propylbenzene, hexylbenzene, heptane, and toluene; ketones such as acetone, 2-butanone, and 2-heptanone; acetonitrile; and dimethyl suifoxide; or a mixture of two or more solvents stated above.

The resulting compound of Formula (I) may be further purified by recrystallization. A solvent used for the recrystallization is a solvent selected from water; alcohols such as methanol, ethanol, propanol, isopropanol, butanol, ethylene glycol, and 1-hexanol; ethers such as tetrahydrofuran, t-butylmethyl ether, cyclopentylmethyl ether, 1,2-dimethoxyethane, and diisopropyl ether; esters such as ethyl acetate, propyl acetate, and hexyl acetate; amides such as N,N-dimethylformamide, N,N-dimethylacetamide, N-methylpyrrolidone, and N,N-dibutylformamide; halogenated hydrocarbons such as 1-chlorohexane; hydrocarbons such as n-propylbenzene, hexylbenzene, heptane, and toluene; ketones such as acetone, 2-butanone, and 2-heptanone; acetonitrile; and dimethyl sulfoxide; or a mixture of two or more solvents stated above.

In another embodiment of the present invention, a high-purity compound of Formula (I) wherein n is 0, m is 0 or 1, and $R^2$ is $C_{1-4}$alkyl is produced. In another embodiment of the present invention, a crystal of a high-purity compound of Formula (I) wherein n is 0, m is 0 or 1, and $R^2$ is $C_{1-4}$alkyl is produced.

A process of the present invention comprising Steps d) to f) enables to prepare a high-purity compound of Formula (I) without a purification procedure requiring cumbersome operations and a large amount of solvents and absorbent, such as column chromatography. Therefore, the process is advantageous from the viewpoint of enhancing production efficiency and of reducing production costs. A method for removing impurities from a compound used as a medicament is very important, and therefore the process of the present invention is useful for stably supplying safe medicaments.

According to further aspect of the present invention, there is provided a compound represented by Formula (IVb):

[Formula 13]

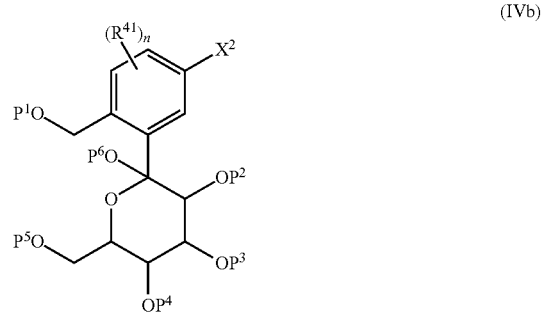

(IVb)

wherein $R^{41}$, n, $X^2$, $P^1$, $P^2$, $P^3$, $P^4$, $P^5$, and $P^6$ are as defined above. The compound is useful as a synthetic intermediate for a compound of Formula (I).

According to further aspect of the present invention, there is provided a compound of Formula (VI):

[Formula 14]

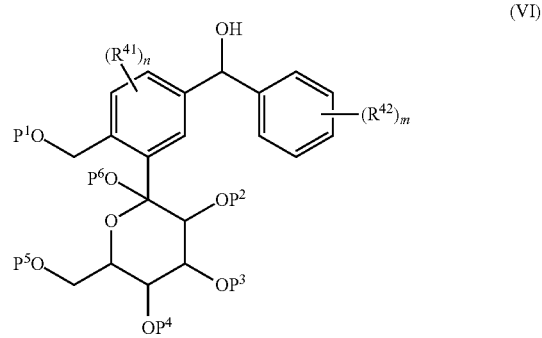

(VI)

wherein $R^{41}$, $R^{42}$, m, n, $P^1$, $P^2$, $P^3$, $P^4$, $P^5$, and $P^6$ are as defined above. The compound is also useful as a synthetic intermediate for a compound of Formula (I).

According to further aspect of the present invention, there is provided a crystal of a compound of Formula (XI):

[Formula 15]

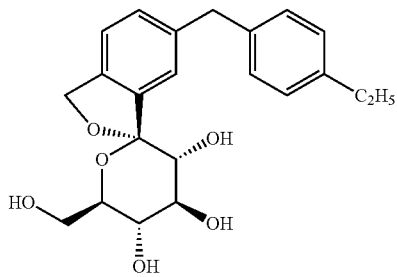

(XI)

In one embodiment of the present invention, the crystal is a monohydrate. Herein, a monohydrate is not limited particularly as long as a crystal stably keeps a moisture in an amount of about 1 equivalent under a condition (e.g. temperature, relative humidity and the like) in which medicaments are commonly used or stored. In one embodiment of this aspect, the crystal is provided as co-crystal with sodium acetate or potassium acetate. In another embodiment of the present invention, there is provided a monohydrate crystal of a high-purity compound of Formula (XI).

A monohydrate crystal of the present invention is characterized in having peaks at diffraction angles (2θ) of about 3.5°, 6.9°, and 13.8°; specifically, about 3.5°, 6.9°, 13.8°, 16.0°, 17.2°, and 18.4°; more specifically, about 3.5°, 6.9°, 10.4°, 13.8°, 16.0°, 17.2°, 18.4°, 20.8°, 21.4°, and 24.4° in X-ray powder diffraction pattern. A co-crystal with sodium acetate of the present invention is characterized in having peaks at diffraction angles (2θ) of about 4.9°, 14.7°, 16.0°, 17.1° and 19.6°; more specifically about 4.9°, 8.7°, 9.3°, 11.9°, 12.9°, 14.7°, 16.0°, 17.1°, 17.7°, 19.6°, 21.6° and 22.0° in X-ray powder diffraction pattern. A co-crystal with potassium acetate of the present invention is characterized in having peaks at diffraction angles (2θ) of about 5.0°, 15.1°, 19.0°, 20.1° and 25.2°; more specifically, about 5.0°, 10.0°, 10.4°, 12.4°, 14.5°, 15.1°, 19.0°, 20.1°, 21.4° and 25.2° in X-ray powder diffraction pattern. Herein, a X-ray powder diffraction pattern can be measured in a common method. Regarding diffraction angle values of X-ray powder diffraction peaks of the crystal of the present invention, some errors (for example, about ±0.2) may be observed by measurement conditions and status of samples.

The monohydrate crystal of the present invention may be obtained by crystallization from a solvent selected from water, or a mixture of methanol and water, ethanol and water, acetone and water, or 1,2-dimethoxyethane and water. For example, the crystallization can be carried out by using a mixture of acetone and water wherein the mixing ratio is preferably acetone water=1:3.5 to 1:7 by volume, more preferably acetone: water=1:4 to 1:7 by volume.

The co-crystal with sodium acetate of the present invention may be obtained by crystallization from a solvent selected from methanol, isopropanol, 1-hexanol acetonitrirle, ethyl acetate, propyl acetate, hexyl acetate, 2-butanone, 2-heptanone, n-propylbenzene, hexylbenzene, and 1-chlorohexane, or a mixture of two or more solvents stated above, preferably from a mixture of methanol and isopropanol.

The co-crystal with potassium acetate of the present invention may be obtained by crystallization from a solvent selected from methanol, isopropanol, 1-hexanol, acetonitrile, ethyl acetate, N,N-dibutylformamide, acetone, and diisopropyl ether, or a mixture of two or more solvents stated above, preferably from a mixture of methanol and isopropanol.

The monohydrate crystal of the present invention has a property that a moisture content is maintained substantially constant under a certain range of relative humidity and that it is easy to handle the compound in formulation process. Further, the monohydrate crystal and the co-crystals with sodium acetate and potassium acetate of the subject invention are useful for preparing a pharmaceutical formulation having excellent stability in storage. Furthermore, the monohydrate crystal and the co-crystals with sodium acetate and potassium acetate can be used for efficiently and highly purifying a compound of Formula (XI), and therefore the crystal is also useful from the viewpoint of efficient preparation of a medicament containing the compound.

DESCRIPTION OF EMBODIMENTS

Examples

Figure 1:
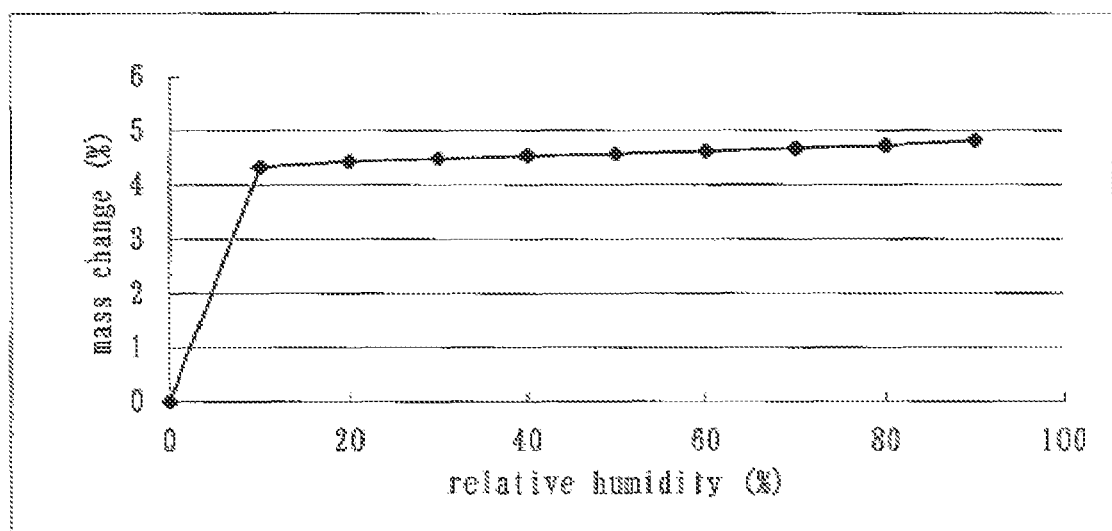
FIG. 1 shows one example of measurement results of water adsorption isotherm measured in Test Example 1.

Preferred examples of the present invention will now be described in more detail. However, the present invention shall not be limited to these examples.

NMR analysis was carried out with nuclear magnetic resonance apparatus: JNM-ECP-500 or JNM-ECP-400 (manufactured by JOEL). Mass spectrum analysis was carried out with mass spectrometer: LCT Premier XE (manufactured by Waters). Preparative high performance liquid chromatography was carried out with GL-Science preprative isolation system. High performance liquid chromatography was carried out with Agilent 1100 (manufactured by Agilent). Moisture analysis was carried out with KF analysis apparatus: Type KF-100 (trace moisture measuring apparatus manufactured by Mitsubishi Chemical Corporation). When a resulting product was used in the next step without purification, a portion of the product or another product prepared separately by the same manner was purified appropriately for measurement of NMR.

Example 1

Synthesis of 1,1-anhydro-1-C-[5-(4-ethylphenyl)methyl-2-(hydroxymethyl)phenyl]-β-D-glucopyranose Step 1: Synthesis of 3,4,5-tris(trimethylsilyloxy)-6-trimethylsilyloxymethyl-tetrahydropyran-2-one

[Formula 16]

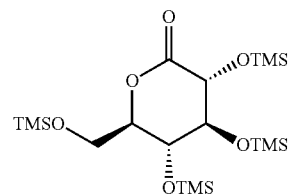

To a solution of D-(+)-glucono-1,5-lactone (7.88 kg) and N-methylmorpholine (35.8 kg) in tetrahydrofuran (70 kg) was added trimethylsilyl chloride (29.1 kg) at 40° C. or below, and then the mixture was stirred at a temperature from 30° C. to 40° C. for 2 hours. After the mixture as cooled to 0° C., toluene (34 kg) and water (39 kg) were added thereto. The organic layer was separated and washed with an aqueous solution of 5% sodium dihydrogen phosphate (39.56 kg×2) and water (39 kg×1). The solvent was evaporated under reduced pressure to give the titled compound as an oil. The product was used in the next step without further purification.

$^1$H-NMR (CDCl$_3$) δ:0.13 (9H, s), 0.17 (9H, s), 0.18 (9H, s), 0.29 (9H, s), 3.74-3.83 (3H, m), 3.90 (1H, t, J=8.0 Hz), 3.99 (1H, d, J=8.0 Hz), 4.17 (1H, dt, J=2.5, 8.0 Hz).

Step 2: Synthesis of 2,4-dibromo-1-(1-methoxy-1-methylethoxymethyl)benzene

[Formula 17]

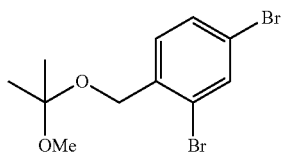

Under a nitrogen atmosphere, to a solution of 2,4-dibromobenzyl alcohol (40 g, 0.15 mol) in tetrahydrofuran (300 ml) was added 2-methoxypropene (144 ml, 1.5 mol) at room temperature and then the mixture was cooled to 0° C. At the same temperature, pyridinium p-toluenesulfonic acid (75 mg, 0.30 mmol) was added and the mixture was stirred for 1 hour. The reaction mixture was poured into a saturated aqueous solution of sodium hydrogen carbonate cooled to 0° C., and extracted with toluene. The organic layer was washed with a saturated aqueous solution of sodium chloride, dried over anhydrous sodium sulfate, and the solvent was evaporated under reduced pressure to give the titled compound as an oil in quantitative yield. The product was used in the next step without further purification.

$^1$H-NMR (CDCl$_3$) δ: 1.44 (6H, s), 3.22 (3H, s), 4.48 (2H, s), 7.42 (1H, d, J=8.0 Hz), 7.44 (1H, dd, J=1.5, 8.0 Hz), 7.68 (1H, d, J=1.5 Hz).

Step 3: Synthesis of 2,3,4,5-tetrakis(trimethylsilyloxy)-6-trimethylsilyloxymethyl-2-(5-(4-ethylphenyl)hydroxymethyl-2-(1-methoxy-1- methylethoxymethyl)phenyl)tetrahydropyran

[Formula 18]

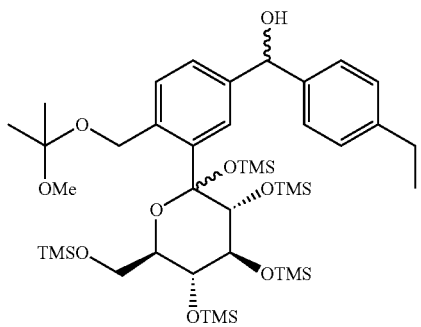

Under a nitrogen atmosphere, 2,4-dibromo-1-(1-methoxy-1-methylethoxymethyl)benzene (70 g, 207 mmol), which was obtained in the previous step, was dissolved in toluene (700 mL) and t-butylmethyl ether (70 ml), and n-butyllithium in hexane (1.65 M, 138 ml, 227 mmol) was added dropwise at 0° C. over 30 minutes. After the mixture was stirred for 1.5 hours at 0° C., the mixture was added dropwise to a solution of 3,4,5-tris(trimethylsilyloxy)-6-trimethylsilyloxymethyltetrahydropyran-2-one (Example 1, 108 g, 217 mol) in tetrahydrofuran (507 ml) at −78° C., and the reaction mixture was stirred for 2 hours at the same temperature. Triethylamine (5.8 ml, 41 mmol) and trimethylsilyl chloride (29.6 ml, 232 mmol) were added thereto, and the mixture was warmed to 0° C. and stirred for 1 hour to give a solution containing 2,3,4,5-tetrakis(trimethylsilyloxy)-6-trimethylsilyloxymethyl-2-(5-bromo-2-(1-methoxy-1-methylethoxymethyl)phenyl)tetrahydropyran.

The resulting solution was cooled to −78° C., and n-butyllithium in hexane (1.65 M, 263 ml, 434 mmol) was added dropwise thereto at the same temperature. After the mixture was stirred at −78° C. for 30 minutes, 4-ethylbenzaldehyde (62 ml, 455 mmol) was added dropwise at −78° C., and the mixture was stirred at the same temperature for 2 hours. A saturated aqueous solution of ammonium chloride was added to the reaction mixture, and the organic layer was separated, and washed with water. The solvent was evaporated under reduced pressure to give a product containing the titled compound as an oil (238 g). The product was used in the next step without further purification.

A portion of the oil was purified by HPLC (column: Inertsil ODS-3, 20 mm I.D.×250 mm; acetonitrile, 30 mL/min) to give four diastereomers of the titled compound (two mixtures each containing two diastereomers).

Mixture of Diastereomers 1 and 2:
$^1$H-NMR (500 MHz, CDCl$_3$) δ: −0.47 (4.8H, s), −0.40 (4.2H, s), −0.003-0.004 (5H, m), 0.07-0.08 (13H, m), 0.15-0.17 (18H, m), 1.200 and 1.202 (3H, each t, J=8.0 Hz), 1.393 and 1.399 (3H, each s), 1.44 (3H, s), 2.61 (2H, q, J=8.0 Hz), 3.221 and 3.223 (3H, each s), 3.43 (1H, t, J=8.5 Hz), 3.54 (1H, dd, J=8.5, 3.0 Hz), 3.61-3.66 (1H, m), 3.80-3.85 (3H, m), 4.56 and 4.58 (1H, each d, J=12.4 Hz), 4.92 and 4.93 (1H, each d, J=12.4 Hz), 5.80 and 5.82 (1H, each d, J=3.0 Hz), 7.14 (2H, d, J=8.0 Hz), 7.28-7.35 (3H, m), 7.50-7.57 (2H, m).

MS (ESI$^+$): 875 [M+Na]$^+$.

Mixture of Diastereomers 3 and 4:
$^1$H-NMR (500 MHz, toluene-d$_8$, 80° C.) δ: −0.25 (4H, s), −0.22 (5H, s), 0.13 (5H, s), 0.16 (4H, s), 0.211 and 0.214 (9H, each s), 0.25 (9H, s), 0.29 (9H, s), 1.21 (3H, t, J=7.5 Hz), 1.43 (3H, s), 1.45 (3H, s), 2.49 (2H, q, J=7.5 Hz), 3.192 and 3.194 (3H, each s), 3.91-4.04 (4H, m), 4.33-4.39 (2H, m), 4.93 (1H, d, J=14.5 Hz), 5.10-5.17 (1H, m), 5.64 and 5.66 (1H, each s), 7.03 (2H, d, J=8.0 Hz), 7.28-7.35 (3H, m), 7.59-7.64 (1H, m), 7.87-7.89 (1H, m).

MS (ESI$^+$): 875 [M+Na]$^+$.

Step 4: Synthesis of 1,1-anhydro-1-C-[5-(4-ethylphenyl)hydroxymethyl-2-(hydroxymethyl)phenyl]-β-D-glucopyranose

[Formula 19]

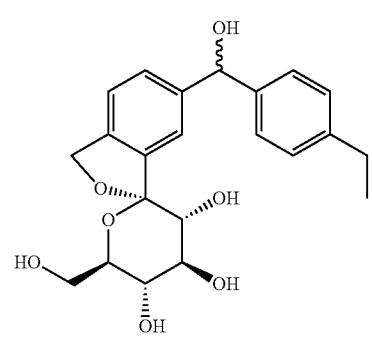

Under a nitrogen atmosphere, the oil containing 2,3,4,5-tetrakis(trimethylsilyloxy)-6-trimethylsilyloxymethyl-2-(5-(4-ethylphenyl)hydroxymethyl-2-(1-methoxy-1-methyl-ethoxymethyl)phenyl)tetrahydropyran (238 g), which was obtained in the previous step, was dissolved in acetonitrile (693 ml). Water (37 ml) and 1N HCl aq (2.0 ml) were added and the mixture was stirred at room temperature for 5.5 hours. Water (693 ml) and n-heptane (693 ml) were added to the reaction mixture and the aqueous layer was separated. The aqueous layer was washed with n-heptane (693 ml×2), and water was evaporated under reduced pressure to give a product countering water and the titled compound (a diastereomer mixture) as an oil (187 g). The product was used in the next step without further purification.

$^1$H-NMR (500 MHz, CD$_3$OD) δ: 1.200 (3H, t, J=7.7 Hz), 1.201 (3H, t, J=7.7 Hz), 2.61 (2H, q, J=7.7 Hz), 3.44-3.48 (1H, m), 3.63-3.68 (1H, m), 3.76-3.84 (4H, m), 5.09 (1H, d, J=12.8 Hz), 5.15 (1H, d, J=12.8 Hz), 5.79 (1H, s), 7.15 (2H, d, J=7.7 Hz), 7.24 and 7.25 (1H, each d, J=8.4 Hz), 7.28 (2H, d, J=32 7.7 Hz), 7.36 (1H, dd, J=8.4, 1.5 Hz), 7.40-7.42 (1H, m).

MS (ESI$^+$): 425 [M+Na]$^+$.

Step 5: Synthesis of 1,1-anhydro-1-C-[5-(4-ethylphenyl)methyl-2-(hydroxymethyl)phenyl]-β-D-glucopyranose (crude product)

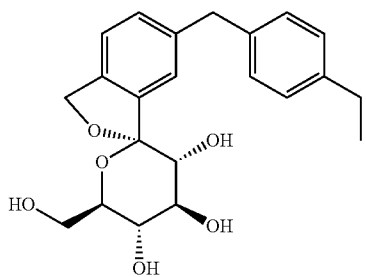

[Formula 20]

To a solution of the oil containing 1,1-anhydro-1-C-[5-(4-ethylphenyl)hydroxymethyl-2-(hydroxymethyl)phenyl]-β-D-glucopyranose (187 g), which was obtained in the previous step, in 1,2-dimethoxyethane (693 ml) was added 5% Pd/C (26 g, 6.2 mmol, water content ratio: 53%), and the mixture was stirred in the atmosphere of hydrogen gas at room temperature for 4 hours. After filtration, the filtrate was evaporated under reduced pressure to give an oil containing the titled compound (59 g). The purity of the resulting product was 85.7%, which was calculated based on the area ratio measured by HPLC. The product was used in the next step without further purification.

$^1$H-NMR (CD$_3$OD) δ: 1.19 (3H, t, J=7.5 Hz), 2.59 (2H, q, J=7.5 Hz), 3.42-3.46 (1H, m), 3.65 (1H, dd, J=5.5, 12.0 Hz), 3.74-3.82 (4H, m), 3.96 (2H, s), 5.07 (1H, d, J=12.8 Hz), 5.13 (1H, d, J=12.8 Hz), 7.08-7.12 (4H, m), 7.18-7.23 (3H, m).

MS (ESI$^+$): 387 [M+1]$^+$.

Measurement Condition of HPLC:

Column: Cadenza CD-C18 50 mm P/NCD032

Mobile phase: Eluent A: H$_2$O, Eluent B: MeCN

Gradient operation: Eluent B: 5% to 100% (6 min), 100% (2 min)

Flow rate: 1.0 mL/min

Temperature: 35.0° C.

Detection wavelength: 210 nm

Step 6: Synthesis of 1,1-anhydro-1-C-[5-(4-ethylphenyl)methyl-2-(hydroxymethyl phenyl]-2,3,4,6-tetra-O-methoxycarbonyl-β-D-glucopyranose

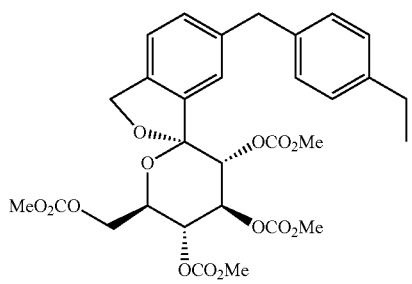

[Formula 21]

Under a nitrogen atmosphere, to a solution of the oil containing 1,1-anhydro-1-C-[5-(4-ethylphenyl)methyl-2-(hydroxymethyl)phenyl]-β-D-glucopyranose (59 g) and 4-(dimethylamino)pyridine (175 g, 1436 mmol) in acetonitrile (1040 ml) was added dropwise methyl chloroformate (95 ml, 1231 mmol) at 0° C. The mixture was allowed to warm to room temperature while stirred for 3 hours. After addition of water, the mixture was extracted with isopropyl acetate. The organic layer was washed with an aqueous solution of 3% potassium hydrogensulfate and 20% sodium chloride (three times) and an aqueous solution of 20% sodium chloride, dried over anhydrous sodium sulfate, and the solvent was evaporated under reduced pressure. To the resulting residue was added ethanol (943 mL) and the mixture was heated to 75° C. to dissolve the residue. The mixture was cooled to 60° C. and a seed crystal of the titled compound was added thereto. The mixture was cooled to room temperature and stirred for 1 hour. After precipitation of solid was observed, water (472 ml) was added thereto, and the mixture was stirred at room temperature for 2 hours. The resulting crystal was collected by filtration, washed with a mixture of water and ethanol (1:1), and dried under reduced pressure to give the titled compound (94 g). To the product (91 g) was added ethanol (1092 ml), and the product was dissolved by heating to 75° C. The solution was cooled to 60° C. and a seed crystal of the titled compound was added thereto. The mixture was cooled to room temperature and stirred for 1 hour. After precipitation of solid was observed, water (360 ml) was added thereto, and the mixture was stirred at room temperature for 2 hours. The resulting crystal was collected by filtration, washed with a mixture of water and ethanol (1:1), and dried under reduced pressure to give the titled compound [83 g, total yield from 2,4-dibromo-1-(1-methoxy-1-methylethoxymethyl)benzene used in Step 3: 68%].

$^1$H-NMR (CDCl$_3$) δ: 1.20 (3H, t, J=7.5 Hz), 2.60 (2H, q, J=7.5 Hz), 3.50 (3H, s), 3.76 (3H, s), 3.77 (314, s), 3.81 (3H, s), 3.96 (2H, s), 4.23 (1H, dd, J=2.5, 11.8 Hz), 4.33 (1H, dd, J=4.5, 12.0 Hz), 4.36-4.40 (1H, m), 5.11-5.20 (3H, m), 5.41 (1H, d, J=10.0 Hz), 5.51 (1H, t, J=10.0 Hz), 7.07-7.11 (4H, m), 7.14 (1H, d, J=7.5 Hz), 7.19 (1H, dd, J=1.5, 7.8 Hz), 7.31 (1H, d, J=1.5 Hz).

MS (ESI$^+$): 619 [M+1]$^+$, 636 [M+18]$^+$.

Another preparation was carried out in the same manner as Step 6, except that a seed crystal was not used, to give the titled compound as a crystal.

Step 7: Synthesis of 1,1-anhydro-1-C-[5-(4-ethylphenyl)methyl-2-(hydroxymethyl)phenyl]-β-D-glucopyranose

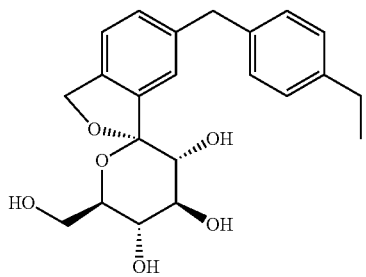

[Formula 22]

To a solution of 1,1-anhydro-1-C-[5-(4-ethylphenyl)methyl-2-(hydroxymethyl)phenyl]-2,3,4,6-tetra-O-methoxycarbonyl-β-D-glucopyranose (8.92 kg as wet powder, corresponding to 8.00 kg of dry powder) in 1,2-dimethoxyethane (28 kg) was added a solution of sodium hydroxide (4 mol/L, 30.02 kg) at 20° C., and the mixture was stirred for 1 hour. Water (8.0 kg) was added to the mixture and the layers were separated. To the organic layer were added an aqueous solution of 25% sodium chloride (40 kg) and ethyl acetate (36 kg). The organic layer was separated, washed with an aqueous solution of 25% sodium chloride (40 kg), and the solvent was evaporated under reduced pressure. The purity of the resulting residue was 98.7%, which was calculated based on the area ratio measured by HPLC. To the resulting residue were added acetone (32.0 kg) and water (0.8 kg), and the solvent was evaporated under reduced pressure. To the resulting residue were added acetone (11.7 kg) and water (15.8 kg), and the solution was cooled to 5° C. or below. Water (64 kg) was added to the solution at 10° C. or below, and the mixture was stirred at the same temperature for 1 hour. The resulting crystal was collected by centrifugation, and washed with a mixture of acetone (1.3 kg) and water 8.0 kg). The resulting wet powder was dried by ventilation drying under a condition at air temperature of 13 to 16° C. and relative humidity of 24% to 33% for 8 hours, to give a monohydrate crystal (water content: 4.502%) of the titled compound (3.94 kg). The purity of the resulting compound was 99.1%, which was calculated based on the area ratio measured by HPLC.

$^1$H-NMR (CD$_3$OD) δ: 1.19 (3H, t, Jβ7.5 Hz), 2.59 (2H, q, J=7.5 Hz), 3.42-3.46 (1H, m), 3.65 (1H, dd, J=5.5, 12.0 Hz), 3.74-3.82 (4H, m), 3.96 (2H, s), 5.07 (1H, d, J=12.8 Hz), 5.13 (1H, d, J=12.8 Hz), 7.08-7.12 (4H, m), 7.18-7.23 (3H, m).

MS (ESI$^+$): 387 [M+1]$^+$.

Measurement Condition of HPLC:
Column: Capcell pack ODS UG-120 (4.6 mm I.D.×150 mm, 3 μm, manufactured by Shiseido Co., Ltd.)
Mobile phase: Eluent A: H$_2$O, Eluent B: MeCN
Mobile phase sending: Concentration gradient was controlled by mixing Eluent A and Eluent B as indicated in the following table.

TABLE 1

| Time from injection (min) | Eluent A (%) | Eluent B (%) |
|---|---|---|
| 0 to 15 | 90→10 | 10→90 |
| 15 to 17.5 | 10 | 90 |
| 17.5 to 25 | 90 | 10 |

Flow rate: 1.0 mL/min
Temperature: 25.0° C.
Detection wavelength: 220 nm
Method for Measurement of Water Content:
Analysis method: coulometric titration method
KF analysis apparatus: Type KF-100 (trace moisture measuring apparatus manufactured by Mitsubishi Chemical Corporation)
Anode solution: Aquamicron AX (manufactured by Mitsubishi Chemical Corporation)
Cathode solution: Aquamicron CXU (manufactured by Mitsubishi Chemical Corporation)

Example 2

Synthesis of 2,3,4,5-tetrakis(trimethylsilyloxy)-6-trimethylsilyloxymethyl-2-(5-bromo-2-(1-methoxy-1-methylethoxymethyl)phenyl)tetrahydropyran

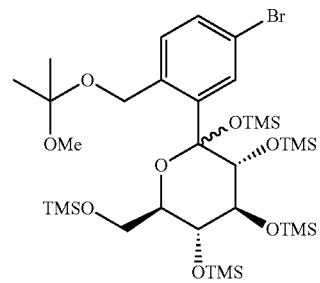

[Formula 23]

According to the procedure of Example 1, Step 3, 2,4-dibromo-1-(1-methoxy-1-methylethoxymethyl)benzene was treated with n-butyllithium in hexane, 3,4,5-tris(trimethylsilyloxy)-6-trimethylsilyloxymethyl-tetrahydropyran-2-one, triethylamine, and trimethylsilyl chloride. The reaction mixture was subjected to workup procedure, and the resulting residue was purified by HPLC (column; Inertsil ODS-3, 20 mm I.D.×250 mm; acetonitrile, 30 mL/min) to give the titled compound as two isolated diastereomers.

Diastereomer 5:

$^1$H-NMR (500 MHz, CDCl$_3$) δ: −0.30 (9H, s), 0.095 (9H, s), 0.099 (9H, s), 0.16 (9H, s), 0.17 (9H, s), 1.41 (3H, s), 1.43 (3H, s), 3.20 (3H, s), 3.37-3.44 (2H, m), 3.62 (1H, dd, J=10.5, 7.5 Hz), 3.81-3.89 (3H, m), 4.62 (1H, d, J=13.2 Hz), 4.81 (1H, d, J=13.2 Hz), 7.38 (1H, dd, J=8.8, 2.5 Hz), 7.46 (1H, d, J=8.8 Hz), 7.70 (1H, d, J=2.5 Hz).

MS (ESI$^+$):819[M+Na]$^+$.

Diastereomer 6:

$^1$H-NMR (500 MHz, toluene-d$_8$, 80° C.) δ: −0.16 (9H, s), 0.18 (9H, s), 0.22 (9H, s), 0.23 (9H, s), 0.29 (9H, s), 1.405 (3H, s), 1.412 (3H, s), 3.16 (3H, s), 3.87 (1H, dd, J=10.5, 4.3 Hz), 3.98 (1H, dd, J=4.3, 1.5 Hz), 4.02 (1H, dd, J=10.5, 2.5 Hz), 4.14 (1H, s), 4.26 (1H, brs), 4.38 (1H, brs), 4.90-4.96 (2H, m), 7.34 (1H, dd, J=8.5, 1.5 Hz), 7.70 (1H, d, J=8.5 Hz), 7.97 (1H, s, brs).

MS (ESI$^+$): 819 [M+Na]$^+$.

Example 3

Synthesis of 1,1-anhydro-1-C-[5-(4-ethylphenyl) methyl-2-(hydroxymethyl)phenyl]-2,3,4,6-tetra-O-pivaloyl-β-D-glucopyranose

[Formula 24]

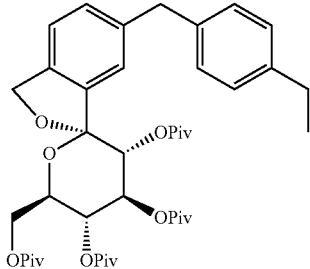

To a solution of 1,1-anhydro-1-C-[5-(4-ethylphenyl)methyl-2-(hydroxymethyl)phenyl]-β-D-glucopyranose monohydrate (3.95 g, 9.77 mmol) and 4-(dimethylamino)pyridine (8.36 g, 68.4 mmol) in dichloromethane (40 ml) was added dropwise pivaloyl chloride (7.8 ml, 63.5 mmol) under cooling with ice bath, and the mixture was stirred at room temperature for about 24 hours. Water was added and the resulting mixture was extracted with hexane. The organic layer was washed with water, a saturated aqueous solution of sodium hydrogen carbonate, and a saturated aqueous solution of sodium chloride sequentially, and the solvent was evaporated under reduced pressure. The resulting residue was purified by silica gel column chromatography (silica gel 150 g, hexane: ethyl acetate=20:1 to 10:1) to give an oil material (7.74 g). The oil material (500 mg) was dissolved in isopropanol (4 ml). Water (1.5 ml) and isopropanol (1 ml) were added sequentially at room temperature and the mixture was stirred for 1 hour. Water (0.5 ml) was added and the mixture was further stirred for 1 hour. Further the mixture was stirred at 0° C. for 1 hour, and the crystal precipitated was collected by filtration, washed with a mixture of water and isopropanol (1:1, 4 ml), and dried to give the titled compound (403 mg).

$^1$H-NMR (CDCl$_3$) δ: 0.71 (9H, s), 1.11 (9H, s), 1.17 (9H, s), 1.20 (9H, s), 1.20 (3H, t, J=7.5 Hz), 2.60 (2H, q, J=7.5 Hz), 3.93 (2H, s), 4.09 (1H, dd, J=4.0, 12.5 Hz), 4.16 (1H, dd, J=2.0, 12.5 Hz), 4.37 (1H, ddd, J=2.0, 4.0, 10.0 Hz), 5.12 (1H, d, J=12.2 Hz), 5.21 (1H, d, J=12.2 Hz), 5.37 (1H, t, J=10.0 Hz), 5.57 (1H, d, J=10.0 Hz), 5.69 (1H, t, J=10.0 Hz), 7.07 (2H, d, J=8.2 Hz), 7.10 (2H, d, J=8.2 Hz), 7.11 (1H, d, J=8.0 Hz), 7.17 (1H, dd, J=1.2, 8.0 Hz), 7.25 (1H, brs).

MS (ESI$^+$): 723 [M+1]$^+$.

Example 4

Synthesis of 3,4,5-tris(trimethylsilyloxy)-6-trimethylsilyloxymethyl-tetrahydropyran-2-one

[Formula 25]

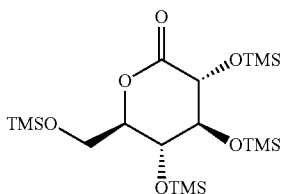

To a solution of D-(+)-glucono-1,5-lactone (21.6 kg) and N-methylmorpholine (98.2 kg) in tetrahydrofuran (192 kg) was added trimethylsilyl chloride (79.1 kg) at 40° C. or below, and then the mixture was stirred at a temperature from 30° C. to 40° C. for 4 hours. After the mixture was cooled to 17° C., toluene (93.6 kg) and water (109 kg) were added thereto. The organic layer was separated and washed with an aqueous solution of 5% sodium dihydrogen phosphate (108 kg×2) and water (108 kg×1). The solvent was evaporated under reduced pressure. To the resulting residue was added tetrahydrofuran (154 kg) and the solvent was evaporated under reduced pressure. Again tetrahydrofuran (154 kg) was added thereto and evaporated under reduced pressure. The resulting residue was dissolved in tetrahydrofuran (253 kg) to give a solution of the titled compound in tetrahydrofuran. The purity of the product was 99.0% (conversion rate: 99.1%), which was calculated based on the area ratio measured by HPLC.

Measurement condition of HPLC:

Column: YMC-Pack ODS-AM 4.6 mm I.D.×150 mm, 3 µm (YMC)

Mobile phase: Eluent A: 2 mM AcONH$_4$/H$_2$O,

Eluent B: 50% (v/v) MeCN/MeOH

Gradient operation: Eluent B: 50% to 95% (15 min), 95% (15 min), 95% to 100% (5 min), and 100%(15 min)

Flow rate: 1.0 mL/min

Column temperature: 40° C.

Detection wavelength: 200 nm

Example 5

Synthesis of 1,1-anhydro-1-C-[5-(4-ethylphenyl) methyl-2-(hydroxymethyl)phenyl]-β-D-glucopyranose Step 1: Synthesis of 2,3,4,5-tetrakis(trimethylsilyloxy)-6-trimethylsilyloxymethyl-2-(5-(4-ethylphenyl)hydroxymethyl-2-(1-methoxy-1-methylethoxymethyl)phenyl)tetrahydropyran

[Formula 26]

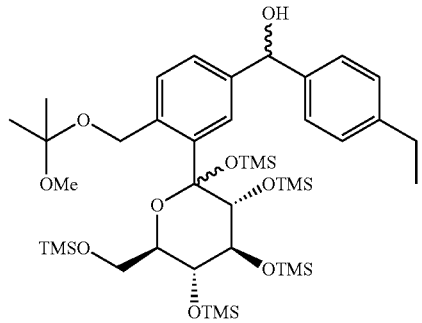

Under an argon atmosphere, 2,4-dibromo-1-(1-methoxy-1-methylethoxymethyl)benzene (277 g, 820 mmol) was dissolved in toluene (2616 mL) and t-butylmethyl ether (262 ml), and n-butyllithium in hexane (1.54 M, 426 ml, 656 mmol) was added dropwise at −10° C. After the mixture was stirred for 0.5 hours at −10° C., n-butyllithium in hexane (1.54M, 160 ml, 246 mmol) was added dropwise at −10° C. After the mixture was stirred for 1 hour at −10° C., in order to confirm the regioselectivity of the halogen-metal exchange reaction, a small portion of the reaction mixture was taken, and added to a saturated aqueous solution of ammonium chloride. The ratio of 4-bromo-1-(1-methoxy-1-methylethoxymethyl)benzene and 2-bromo-1-(1-methoxy-1-methylethoxymethyl)benzene included in the resulting mixture was 53:1 (conversion rate: 98%), which was calculated based on the area ratio measured by HPLC.

After the reaction mixture was cooled to −48° C., the mixture was added dropwise to a solution of 3,4,5-tris(trimethylsilyloxy)-6-trimethylsilyloxymethyl-tetrahydropyran-2-one (402 g, 862 mmol) in tetrahydrofuran (2012 ml) at −77° C., and the reaction mixture was stirred at −70° C. for 1.5 hours. Triethylamine (24 ml, 172 mmol) and trimethylsilyl chloride (98 g, 903 mmol) were added thereto, and the mixture was warmed to 0° C. to give a solution containing 2,3,4,5-tetrakis(trimethylsilyloxy)-6-trimethylsilyloxymethyl-2-(5-bromo-2-(1-methoxy-1-methylethoxymethyl)phenyl) tetrahydropyran. The resulting solution was cooled to −78° C., and n-butyllithium in hexane (1.54 M, 1119 ml, 1724 mmol) was added dropwise thereto at the same temperature. After the mixture was stirred for 1 hour, 4-ethylbenzaldehyde (242 g, 1806 mmol) was added dropwise at −78° C., and the mixture was stirred at the same temperature for 2.5 hours. The reaction mixture was poured into an aqueous solution of 20% ammonium chloride, and the organic layer was separated, and washed with water. The solvent was evaporated under reduced pressure to give a product containing the titled compound as an oil (879 g). The product was used in the next step without further purification.

Measurement condition of HPLC:
Column: Ascentis Express C18, 3.0 mm I.D.×100 mm, 2.7 μm (Supelco)
Mobile phase: Eluent A: 2 mM AcONH$_4$/H$_2$O,
Eluent B: MeCN
Gradient operation: Eluent B: 30% to 98% (25 min), 98% (5 min)
Flow rate: 1.0 mL/min Column temperature: 40° C.
Detection wavelength: 210 nm Step 2: Synthesis of 1,1-anhydro-1-C-[5-(4-ethylphenyl) hydroxymethyl-2-(hydroxymethyl)phenyl]-β-D-glucopyranose

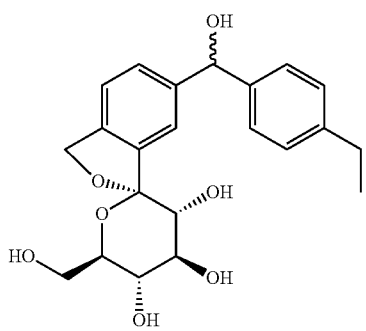

[Formula 27]

Under a nitrogen atmosphere, the oil containing 2,3,4,5-tetrakis(trimethylsilyloxy)-6-trimethylsilyloxymethyl-2-(5-(4-ethylphenyl)hydroxymethyl-2-(1-methoxy-1-methylethoxymethyl)phenyl)tetrahydropyran (628 g), which was a portion of the product obtained in the previous step, was dissolved in tetrahydrofuran (991 ml). Water (63 ml) and 1N HCl aq (23 ml) were added and the mixture was stirred at 28° C. for 7 hours. Triethylamine (3.8 ml, 25.8 mmol) was added to the reaction mixture, and the solvent was evaporated under reduced pressure. Water (198 ml) and 1,2-dimethoxyethane (396 ml) were added to the residue and the two layers were separated. The aqueous layer was washed with n-heptane (595 ml). Water (99 ml) and 1,2-dimethoxyethane (198 ml) were added to the aqueous layer. The mixture was washed with n-heptane (595 ml), and the aqueous layer was concentrated under reduced pressure. To the resulting residue was added 1,2-dimethoxyethane (793 ml) and the solvent was evaporated under reduced pressure to give an oil countering the titled compound (247 g). The product was used in the next step without further purification.

Step 3: Synthesis of 1,1-anhydro-1-C-[5-(4-ethylphenyl) methyl-2-(hydroxymethyl)phenyl]-βD-glucopyranose

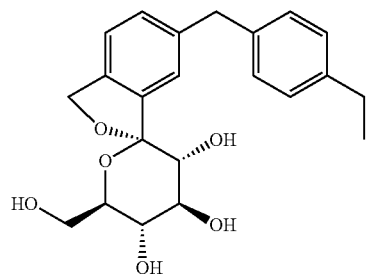

[Formula 28]

To a solution of the oil containing 1,1-anhydro-1-C-[5-(4-ethylphenyl)hydroxymethyl-2-(hydroxymethyl)phenyl]-β-D-glucopyranose (125 g), which was a portion of the product obtained in the previous step, in 1,2-dimethoxyethane (400 ml) were added water (150 ml) and 5% Pd/C (19 g, 4.5 mmol, water content ratio: 50%), and the mixture was stirred in the atmosphere of hydrogen gas at room temperature for 6 hours. The reaction mixture was filtered and the residue was washed with a mixture of 1,2-dimethoxyethane (250 ml) and water (250 ml). The filtrate and the washings were combined and 1,2-dimethoxyethane (500 ml) was added thereto. The mixture was washed with n-heptane (1000 ml×2). Ethyl acetate (500 ml) and an aqueous solution of 25% sodium chloride (600 g) were added to the aqueous layer, and the product was extracted to the organic layer. The separated organic layer was washed with an aqueous solution of 15% sodium chloride (600 g), and the solvent was evaporated under reduced pressure. To the resulting residue was added acetone (500 ml), and the solvent was evaporated under reduced pressure to give the product containing the titled compound (106 g). The purity of the resulting product was 93.9%, which was calculated based on the area ratio measured by HPLC. The product was used in the next step without further purification.

Measurement condition of HPLC:
Column: Atlantis dC18, 4.6 mm I.D.×75 mm, 3 μm (Waters)
Mobile phase: Eluent A: H$_2$O,
Eluent B: MeCN
Gradient operation: Eluent B: 2% to 20% (3 min), 20% to 28% (5 min), 28% (12 min), Eluent B: 28% to 100% (7 min), and 100% (8 min)
Flow rate: 1.2 mL/min
Column temperature: 35° C.
Detection wavelength: 210 nm Step 4: Synthesis of 1,1-anhydro-1-C-[5-(4-ethylphenyl)methyl-2-(hydroxymethyl)phenyl]-2,3,4,6-tetra-O-methoxycarbonyl-β-D-glucopyranose

[Formula 29]

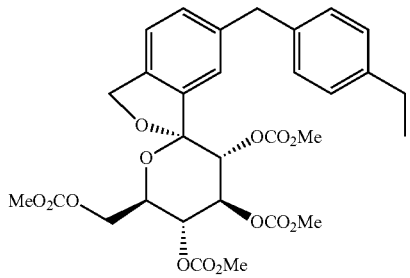

1,1-Anhydro-1-C-[5-(4-ethylphenyl)methyl-2-(hydroxymethyl)phenyl]-β-D-glucopyranose (106 g), which was obtained in the previous step, and 1-methylimidazole (318 ml, 3994 mmol) were dissolved in acetone (400 ml). Under a nitrogen atmosphere, methyl chloroformate (182 ml, 2367 mmol) was added dropwise to the solution at 15° C. The mixture was allowed to warm to 18° C. while stirred for 3 hours. After addition of water (800 ml), the mixture was extracted with ethyl acetate (800 ml). The organic layer was washed with an aqueous solution of 10% potassium hydrogensulfate and 5% sodium chloride (800 ml), and an aqueous solution of 20% sodium chloride (800 ml×2), and then the solvent was evaporated under reduced pressure. To the resulting residue were added ethanol (1200 ml), t-butylmethyl ether (200 ml) and 2-propanol (130 ml). The mixture was heated to 74° C. to dissolve the residue, and then cooled to 55° C. and stirred for 1 hour. After precipitation of solid was observed, the mixture was cooled from 55 to 25° C. over 1.5 hours. 2-Propanol (270 ml) was added thereto, and the mixture was stirred at 25° C. for 1 hour. The resulting crystal was collected by filtration, washed with a mixture of ethanol and 2-propanol (3:1, 300 ml) followed by with a mixture of ethanol and water (1:1, 300 ml) to give the titled compound as wet powder [122 g, corresponding to 104 g of dry powder, total yield from 2,4-dibromo-1-(1-methoxy-1-methylethoxymethyl)benzene used in Step 1: 57%].

Step 5: Synthesis of 1,1-anhydro-1-C-[5-(4-ethylphenyl)methyl-2-(hydroxymethyl)phenyl]-β-D-glucopyranose

[Formula 30]

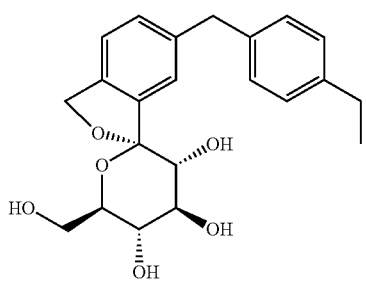

Under a nitrogen atmosphere, to a solution of 1,1-anhydro-1-C-[5-(4-ethylphenyl)methyl-2-(hydroxymethyl)phenyl]-2,3,4,6-tetra-O-methoxycarbonyl-β-D-glucopyranose (96 g as wet powder, corresponding to 82 g of dry powder) in 1,2-dimethoxyethane (328 ml) was added dropwise an aqueous solution of sodium hydroxide (4N, 265 ml, 1060 mmol) at 40° C. The mixture was stirred at the same temperature for 4.5 hours. Water (82 ml) was added to the mixture and the organic layer was separated. The organic layer was washed with an aqueous solution of 18% sodium dihydrogen phosphate dihydrate and 12% disodium hydrogen phosphate dodecahydrate (410 ml) and then ethyl acetate (410 ml) was added thereto. The organic layer was washed with an aqueous solution of 25% sodium chloride (410 ml×2), and the solvent was evaporated under reduced pressure.

To the resulting residue were added acetone (410 ml) and water (8.2 ml) and the solvent was evaporated under reduced pressure. To the resulting residue were added acetone (164 ml) and water (655 ml), and the residue was dissolved by warming to 28° C. The solution was cooled to 25° C. and a seed crystal of the titled compound (82 mg) was added. The mixture was cooled from 25° C. to 20° C. over 24 minutes, and stirred at 20° C. for 1 hour. After precipitation of solid was observed, the mixture was warmed to 25° C. and stirred at the same temperature for 1 hour. Subsequently, the mixture was cooled from 25° C. to −5° C. over 2.4 hours, and the resulting crystal was collected by filtration. Water (246 ml) was added to the resulting crystal and the mixture was stirred at 4° C. for 1 hour. After filtration, the resulting wet powder was dried under reduced pressure (pressure: 1 hPa, outside temperature: 20 to 25° C.) for 20 minutes to give wet powder (water content: 8.249%). The resulting powder was further dried under reduced pressure (pressure: 25 hPa, outside temperature: 20 to 25° C.) for 30 minutes to give the titled compound as a monohydrate crystal (44 g, yield 82%, water content 4.470%). The purity of the resulting compound was 99.9%. Which was calculated based on the area ratio measured by HPLC.

Method for measurement of water content:

Analysis method: coulometric titration method

KF analysis apparatus: Type KF-100 (trace moisture measuring apparatus manufactured by Mitsubishi Chemical Corporation)

Anode solution: Aquamicron AX (manufactured by Mitsubishi Chemical Corporation)

Cathode solution: Aquamicron CXU (manufactured by Mitsubishi Chemical Corporation)

A seed crystal used in Example 5, Step 5 was a portion of the crystal obtained in the following procedure.

1,1-Anhydro-1-C[5-(4-ethylphenyl)methyl-2-(hydroxymethyl)phenyl]-β-D-glucopyranose (180.4 g) was dissolved in water (250 ml) and acetone (250 ml) at 25° C. and insoluble materials were removed by filtration. To the filtrate was added a mixture of water (326 ml) and acetone (326 ml), and the solution was cooled to 4° C. Water (2.31 l) was added thereto with stirring the mixture and keeping it at 11° C. or below, and precipitation of solid was observed. The precipitate was collected by filtration, washed with a mixture of water (289 ml) and acetone (59 ml), and dried by ventilation drying to give a crystal (160.7 g).

Measurement condition of HPLC:

Column: ZORBAX Eclipse XDB-C18, 4.6 mm I.D.×50 mm, 1.8 μm (Agilent)

Mobile phase: Eluent A: $H_2O$,

Eluent B: MeOH

Gradient operation: Eluent B: 40% to 60% (11.5 min), 60% to 80% (7 min), 80% to 95% (4 min), 95% (5 min)

Flow rate: 1.0 ml/min

Column temperature: 50° C.

Detection wavelength: 220 nm

Example 6

Halogen-metal exchange reaction on 2,4-dibromo-1-(1-methoxy-1-methylethoxymethyl)benzene Halogen-metal exchange reactions on 2,4-dibromo-1-(1-methoxy-1-methylethoxymethyl)benzene were carried out in the following conditions (Conditions 1 to 4). The regioselectivity in the reactions was confirmed by $^1$H-NMR analysis.

Condition 1: Under a nitrogen atmosphere, 2,4-dibromo-1-(1-methoxy-1-methylethoxymethyl)benzene (500 mg, 1.48 mmol) was dissolved in toluene (3.65 ml) and t-butylmethyl ether (0.35 ml). To the solution was added dropwise n-butyllithium in hexane (1.6 M, 1.01 ml, 1.62 mmol) at 0° C. over 3 minutes. After completion of the addition, a saturated aqueous solution of ammonium chloride was added thereto, and the mixture was extracted with ethyl acetate. The organic layer was washed with a saturated aqueous solution of sodium chloride, and dried over anhydrous sodium sulfate. The solvent was evaporated under reduced pressure to give a product containing 4-bromo-1-(1-methoxy-1-methylethoxymethyl)benzene, and 2-bromo-1-(1-methoxy-1-methylethoxymethyl)benzene, which may be referred to as 4-bromide and 2-bromide respectively hereinafter, as an oil (376 mg). According to $^1$H-NMR analysis of the product, the ratio of 4-bromide:2-bromide was determined as 16:1, which was calculated based on the integration ratio of peaks of protons at benzyl position (4-bromide: δ4.43 ppm, 2-bromide: δ4.55 ppm).

4-Bromo-1-(1-methoxy-1-methylethoxymethyl)benzene $^1$H-NMR (CDCl$_3$) δ: 1.41 (6H, s), 3.24 (3H, s), 4.43 (2H, s), 7.21-7.24 (2H, m), 7.44-7.47 (2H, m).

2-Bromo-1-(1-methoxy-1-methylethoxymethyl)benzene $^1$H-NMR (CDCl$_3$) δ: 1.46 (6H, s), 3.24 (3H, s), 4.55 (2H, s), 7.10-7.14 (1H, m), 7.29-7.33 (1H, m), 7.51-7.55 (2H, m).

Condition 2: Under a nitrogen atmosphere, 2,4-dibromo-1-(1-methoxy-1-methylethoxymethyl)benzene (500 mg, 1.48 mmol) was dissolved in toluene (3.65 ml) and t-butylmethyl ether (0.35 ml). To the solution was added dropwise n-butyllithium in hexane (1.6 M, 1.01 ml, 1.62 mmol) at 0° C. over 3 minutes. A solution of 2,4-dibromo-1-(1-methoxy-1-methylethoxymethyl)benzene (150 mg, 0.44 mmol) in toluene (1.1 ml) and t-butylmethyl ether (0.11 ml) was added dropwise to the reaction mixture. After completion of the addition, the reaction mixture was stirred at 0° C. for 30 minutes. A saturated aqueous solution of ammonium chloride was added thereto, and the mixture was extracted with ethyl acetate. The organic layer was washed with a saturated aqueous solution of sodium chloride, and dried over anhydrous sodium sulfate. The solvent was evaporated under reduced pressure to give a product containing 4-bromide and 2-bromide as an oil (458 mg). According to $^1$H-NMR analysis of the product, the ratio of 4-bromide:2-bromide was determined as 220:1, which was calculated based on the integration ratio of peaks of protons at benzyl position.

Condition 3: Under a nitrogen atmosphere, 2,4-dibromo-1-(1-methoxy-1-methylethoxymethyl)benzene (150 mg, 0.44 mmol) was dissolved in toluene (1.1 ml) and t-butylmethyl ether (0.11 ml). To the solution was added dropwise n-butyllithium in hexane (1.6 M, 0.3 ml, 0.48 mmol) at 0° C. over 3 minutes. After completion of the addition, the reaction mixture was stirred at 0° C. for 30 minutes. A saturated aqueous solution of ammonium chloride was added thereto, and the mixture was extracted with ethyl acetate. The organic layer was washed with a saturated aqueous solution of sodium chloride, and dried over anhydrous sodium sulfate. The solvent was evaporated under reduced pressure to give a product containing 4-bromide and 2-bromide as an oil (108 mg). According to $^1$H-NMR analysis of the product, the ratio of 4-bromide:2-bromide was determined as 16:1, which was calculated based on the integration ratio of peaks of protons at benzyl position.

Condition 4: Under a nitrogen atmosphere, 2,4-dibromo-1-(1-methoxy-1-methylethoxymethyl)benzene (500 mg, 1.48 mmol) was dissolved in toluene (3.65 ml) and t-butylmethyl ether (0.35 ml). To the solution was added dropwise n-butyllithium in hexane (1.6 M, 1.01 ml, 1.62 mmol) at 0° C. over 30 minutes. After completion of the addition, a saturated aqueous solution of ammonium chloride was added thereto, and the mixture was extracted with ethyl acetate. The organic layer was washed with a saturated aqueous solution of sodium chloride, and dried over anhydrous sodium sulfate. The solvent was evaporated under reduced pressure to give a product containing 4-bromide and 2-bromide as an oil (373 mg). According to $^1$H-NMR analysis of the product, the ratio of 4-bromide:2-bromide was determined as 40:1, which was calculated based on the integration ratio of peaks of protons at benzyl position.

Example 7

Synthesis of 1,1-anhydro-1-C-[5-(4-ethylphenyl)methyl-2-(hydroxymethyl)phenyl]-β-D-glucopyranose To a solution of 1,1-anhydro-1-C-[5-(4-ethylphenyl)methyl-2-(hydroxymethyl)phenyl]-2,3,4,6-tetra-O-methoxycarbonyl-β-D-glucopyranose (88.2 g as wet powder) in 1,2-dimethoxyethane (285 ml) was added a solution of sodium hydroxide (5 M, 285 ml) at room temperature, and the mixture was stirred at the same temperature for 1 hour. After addition of an aqueous solution of sulfuric acid (1 M, 713 ml) to the mixture, water (100 ml) was added thereto, and the mixture was extracted twice with ethyl acetate (500 ml). The combined organic layer was washed with a saturated aqueous solution of sodium chloride (1000 ml), dried over anhydrous sodium sulfate (250 g) and an about half of the solvent was removed under reduced pressure. The resulting precipitate was collected by filtration, and the product was obtained as crystalline powder (10.3 g). A portion of the product (4 mg) was dissolved in dimethyl sulfoxide (0.02 ml). The solution was lyophilized at −20° C. over 2 days to remove dimethyl sulfoxide. Water (0.02 ml) was added to the resulting residue, and a very small portion of the product obtained above was added thereto as a seed crystal. The mixture was shaken at 100 rpm by DOUBLE SHAKER NR-3 (TAITEC) at room temperature for 10 days to give crystal of the titled compound. The resulting crystal is confirmed to be a monohydrate by measurement of powder X-ray diffraction, in which peaks were observed at the same diffraction angles (2θ) as those of the X-ray powder diffraction pattern of the monohydrate measured in Test Example 5.

Example 8

Preparation of co-crystal of 1,1-anhydro-1-C-[5-(4-ethylphenyl)methyl-2-(hydroxymethyl)phenyl]-β-D-glucopyranose with sodium acetate Monohydrate crystal of 1,1-anhydro-1-C-[5-(4-ethylphenyl)methyl-2-(hydroxymethyl)phenyl]β-D-glucopyranose (200 mg) and sodium acetate (40 mg) were dissolved in methanol (1 ml) at 80° C. After the solution was cooled to room temperature, isopropanol (2 ml) was added thereto. The solvent (ca. 2 ml) was removed by evaporation under reduced pressure. A seed crystal of the titled co-crystal was added thereto, and the mixture was stirred at room temperature overnight. Crystal precipitated was collected by filtration, washed with isopropanol (4 ml), and dried to give the titled co-crystal (melting point: 162° C.). By $^1$H-NMR analysis of the resulting co-crystal in $(CD_3)_2SO$, the ratio of the titled compound and sodium acetate in the co-crystal was confirmed as 1:1, which was calculated based on the integration ratio of peaks of protons at $CH_3$ in ethyl of the compound (δ1.12-1.16 ppm (3H, t)) and at $CH_3$ of sodium acetate (δ1.56 ppm (3H, s)).

The seed crystal used in the preparation was obtained in the following procedure. Monohydrate crystal of 1,1-anhydro-1-C-[5-(4-ethylphenyl)methyl-2-(hydroxymethyl)phenyl]-β-D-glucopyranose (8 mg) and sodium acetate (2 mg) were dissolved in methanol (0.1 ml) at 80° C. The solvent was fully evaporated from the solution at 80° C. to give the desired crystalline material.

Measurement condition of melting point:
Analysis method: differential scanning calorimetry (DSC)
Apparatus: DSC6200R (SII NanoTechnology Inc.)
Scanning rate: 10° C./min
Scanning range: 30 to 210° C.
Amount of sample: 3 to 4 mg

Example 9

Preparation of co-crystal of 1,1-anhydro-1-C-[5-(4-ethylphenyl)methyl-2-(hydroxymethyl)phenyl]-β-D-glucopyranose with potassium acetate Monohydrate crystal of 1,1-anhydro-1-C-[5-(4-ethylphenyl)methyl-2-(hydroxymethyl)phenyl]-β-D-glucopyranose (200 mg) and potassium acetate (48 mg) were dissolved in methanol (1 ml) at 80° C. After the solution was cooled to room temperature, isopropanol (2 ml) was added thereto. The solvent (ca. 2 ml) was removed by evaporation under reduced pressure. A seed crystal of the titled co-crystal was added thereto, and the mixture was stirred at room temperature overnight. Crystal precipitated was collected by filtration, washed with isopropanol (4 ml), and dried to give the titled co-crystal (melting point: 176° C.). By $^1$H-NMR analysis of the resulting co-crystal in $(CD_3)_2SO$, the ratio of the titled compound and potassium acetate in the co-crystal was confirmed as 1:1, which was calculated based on the integration ratio of peaks of protons at $CH_3$ in ethyl of the compound (δ1.13-1.16 ppm (3H, t)) and at $CH_3$ of potassium acetate (δ1.53 ppm (3H, s)).

The seed crystal used in the preparation was obtained in the following procedure. Monohydrate crystal of 1,1-anhydro-1-C-[5-(4-ethylphenyl)methyl-2-(hydroxymethyl)phenyl]-β-D-glucopyranose (8 mg) and potassium acetate (2 mg) were dissolved in methanol (0.1 ml) at 80° C. The solvent was fully evaporated from the solution at 80° C. to give the desired crystal. Melting point was measured in the same condition as Example 7.

Test Example 1

Measurement of Water Adsorption Isotherm

Water adsorption isotherm was measured for monohydrate crystal of a compound represented by Formula (XI):

[Formula 31]

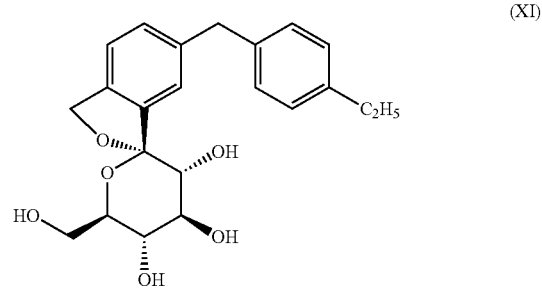 [SMILES: CCc1ccc(Cc2ccc3c(c2)[C@]2(OC3)O[C@H](CO)[C@@H](O)[C@H](O)[C@H]2O)cc1]

(XI)

by using dynamic water absorption isotherm measurement device: DVS-1 (Surface Measurement Systems) as stated below.

Crushed monohydrate crystal of the compound was weighed precisely as a measurement sample (ca. 10 mg, water content: 4.5%) and taken into a sample pan. An empty sample pan was used as a control sample. The measurement sample and the control sample were set in the device. At a constant temperature (around 25° C.), relative humidity (RH) was varied to 90%, 80%, 70%, 60%, 50%, 40%, 30%, 20%, 10%, and 0% in a row, and weight change of the measurement sample was measured. The measurement results were shown in FIG. 1. The results indicate that the compound represented by Formula (XI) exists stably as monohydrate in a range of relative humidity from 10% to 90%.

Test Example 2

Storage Stability Test of Monohydrate Crystal

A storage stability test was carried out for monohydrate crystal and an amorphous form of the compound of Formula (XI). The monohydrate crystal of the compound of Formula (XI) was prepared according to the procedure of Example 1, Step 7. The amorphous form of the compound of Formula (XI) was obtained by the following procedure. The monohydrate crystal of the compound (15 g) was melted by heating on hot-stage, and allowed to be cooled to room temperature in a humidity-controlled desiccator (25° C./dry). The resulting solid was grinded in mortar to give a sample used as an amorphous form. The samples were stored in thermostatic chambers at 25° C. or 40° C., and the purity each of the samples was observed after 1 month, 3 months and 6 months.

The purity was determined in the following procedure. A portion each of the samples was weighed precisely (ca. 6 mg) and dissolved in a mixture of water and methanol (1:1) to be 10 mL accurately. The resulting solutions were used as sample solutions, and a portion (10 μL) each of the sample solutions was subjected to HPLC analysis. A total amount of impurities were calculated according to the following formula.

$$\text{Total amount of impurities (\%)} = \frac{\text{Sum of peak areas each of impurities}}{(\text{Peak area of the compound of formula (XI)}) + (\text{Sum of peak areas each of impurities})} \quad \text{[Formula 32]}$$

Measurement condition of HPLC

Device: 2695 Separations Module (manufactured by Waters), 2487 Dual λ Absorbance Detector (manufactured by Waters) or 996 Photodiode Array Detector (manufactured by Waters)

Column: YMC-Pack ODS-AM AM-302-3, 4.6 mm I.D.× 15 cm, particle size 3 μm (manufactured by YMC)

Mobile phase: Eluent A=methanol, Eluent B=water

Gradient operation: Eluent A: 55% (15 min), Eluent A: 55% to 100% (10 min), 100% (5 min)

Flow rate: 1.0 mL/min

Detection wavelength: 220 nm

Sample cooler temperature: 5° C.

Period for measuring peak area: 30 minutes after injection

The results were shown in Table 2. Both at 25° C. and 40° C., the total amounts of impurities in the amorphous form were increased time-dependently. On the other hand, the total amounts of impurities in the monohydrate crystal were maintained nearly constant for 6 months.

TABLE 2

| Temp. in storage | Form | Total amount of impurities (%) | | | |
|---|---|---|---|---|---|
| | | 0 month | 1 month | 3 month | 6 month |
| 25° C. | Monohydrate crystal | 0.30 | — | 0.29 | 0.32 |
| | Amorphous form | 0.35 | — | 0.66 | 0.87 |
| 40° C. | Monohydrate crystal | 0.30 | 0.32 | 0.31 | 0.36 |
| | Amorphous form | 0.35 | 0.62 | 0.92 | 1.46 |

Test Example 3

Storage Stability Test of Co-Crystal with Sodium Acetate

A storage stability test was carried out for co-crystal of the compound of Formula (XI) with sodium acetate according to the procedure of Test Example 2. The co-crystal of the compound of Formula (XI) with sodium acetate was prepared according to the procedure of Example 5. The samples were stored in thermostatic chambers at 25° C. or 40° C., and the purity each of the samples was observed after 1 month and 3 months. The measurement results were pared with those for the amorphous form obtained in Test Example 2.

The results were shown in Table 3. Both at 25° C. and 40° C., the total amounts of impurities in the amorphous form were increased time-dependently. On the other hand, the total amounts of impurities in the co-crystal with sodium acetate were maintained nearly constant for 3 months.

TABLE 3

| Temp. in storage | Form | Total amount of impurities (%) | | |
|---|---|---|---|---|
| | | 0 month | 1 month | 3 month |
| 25° C. | Co-crystal with sodium acetate | 0.07 | — | 0.07 |
| | Amorphous form | 0.35 | — | 0.66 |
| 40° C. | Co-crystal with sodium acetate | 0.07 | 0.07 | 0.08 |
| | Amorphous form | 0.35 | 0.62 | 0.92 |

Test Example 4

Storage Stability Test of Co-Crystal with Potassium Acetate

A storage stability test was carried out for co-crystal of the compound of Formula (XI) with potassium acetate according to the procedure of Test Example 2. The co-crystal of the compound of Formula (XI) with potassium acetate was prepared according to the procedure of Example 6. The samples were stored in thermostatic chambers at 25° C. or 40° C., and the purity each of the samples was observed after 1 month and 3 months. The measurement results were compared with those for the amorphous form obtained in Test Example 2.

The results were shown in Table 4. Both at 25° C. and 40° C., the total amounts of impurities in the amorphous form were increased time-dependently. On the other hand, the total amounts of impurities in the co-crystal with potassium acetate were maintained nearly constant for 3 months.

TABLE 4

| Temp. in storage | Form | Total amount of impurities (%) | | |
|---|---|---|---|---|
| | | 0 month | 1 month | 3 month |
| 25° C. | Co-crystal with potassium acetate | 0.08 | — | 0.08 |
| | Amorphous form | 0.35 | — | 0.66 |
| 40° C. | Co-crystal with potassium acetate | 0.08 | 0.08 | 0.08 |
| | Amorphous form | 0.35 | 0.62 | 0.92 |

Test Example 5

Powder X-Ray Diffraction Measurement

Powder X-ray diffraction was measured for the monohydrate and amorphous form of the compound of Formula (XI), and for co-crystals of the compound of Formula (XI) with sodium acetate and potassium acetate. The measurement conditions were shown below.

Equipment: RINT 1100 (Rigaku Corporation)
Anticathode: Cu
Tube voltage: 40 kV
Tube current: 40 mA
Scan rate: 2.000 degree/min
Sampling range: 0.020°
Divergence slit: 1°
Scatter slit: 1°
Receiving slit: 0.15 mm
Scan range: 3 to 35°
Measurement conditions for the monohydrate (Condition 2)
Equipment: X'Pert MPD (PANalytical)
Anticathode: Cu
Tube voltage: 45 kV
Tube current: 40 mA
Scan mode: continuous scan
Step width: 0.017
Scan axis: 20
Sampling time per step: 30 sec
Scan range: 2 to 35°

Measurement Conditions for the Amorphous Form
Equipment: RINT 1100 (Rigaku Corporation)
Anticathode: Cu
Tube voltage: 40 kV
Tube current: 20 mA
Scan rate: 2.000 degree/min
Sampling range: 0.020°
Divergence slit: 1°
Scatter slit: 1°
Receiving slit 0.15 mm
Scan range: 2 to 35°
Measurement Conditions for the Co-Crystals with Sodium Acetate and Potassium Acetate
Equipment: X'Pert MPD (PANalytical)
Anticathode: Cu
Tube voltage: 45 kV
Tube current: 40 mA
Scan rate: 1.000 degree/min
Sampling Sampling range:0.050°
Divergence slit: 0.25°
Scatter slit: 0.25°
Receiving slit: 0.2 mm
Scan range: 3 to 35°

Figure 2:
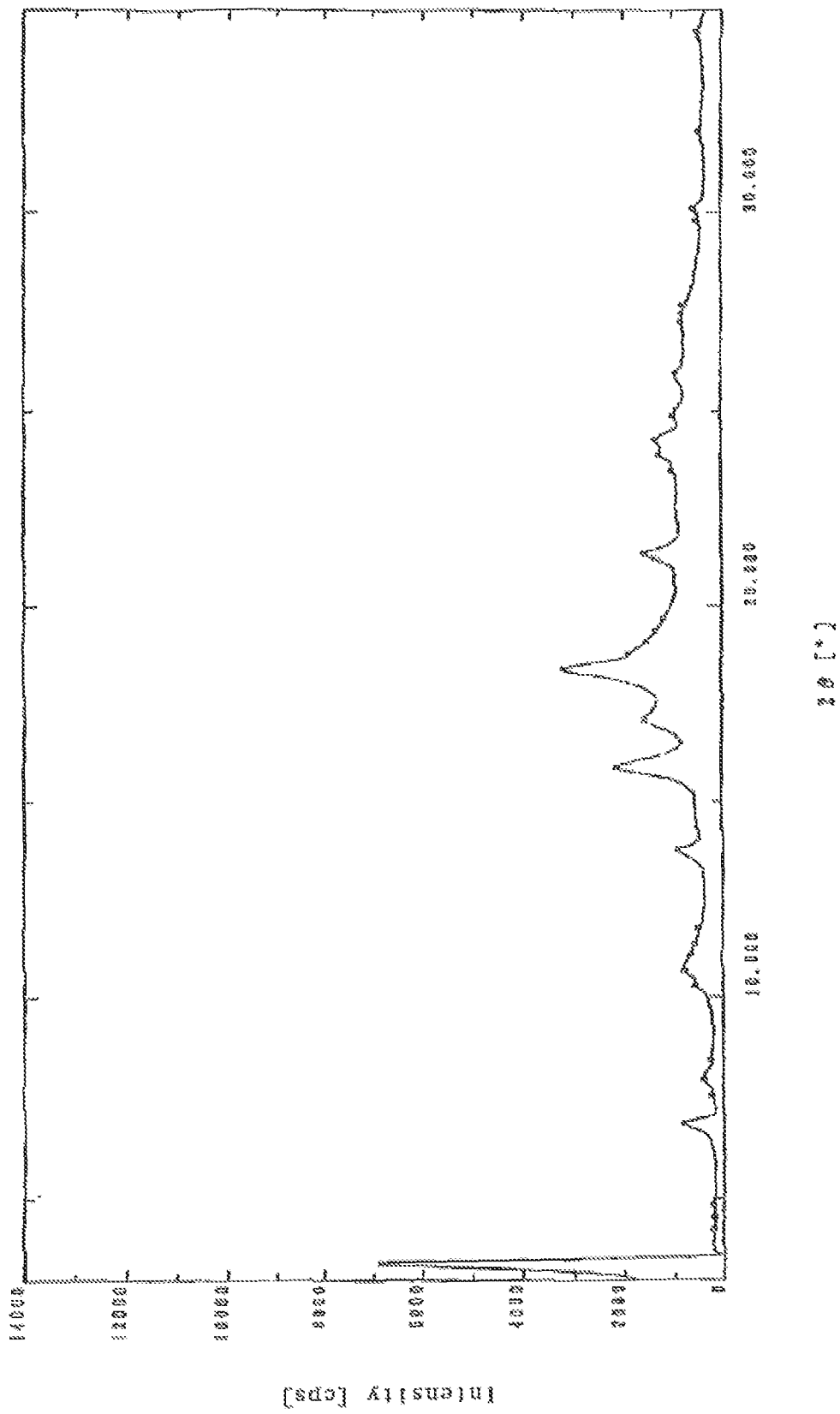
FIG. 2 shows one example of measurement results of powder X-ray diffraction of the monohydrate crystal measured in Test Example 5 (Condition 1).
Figure 3:
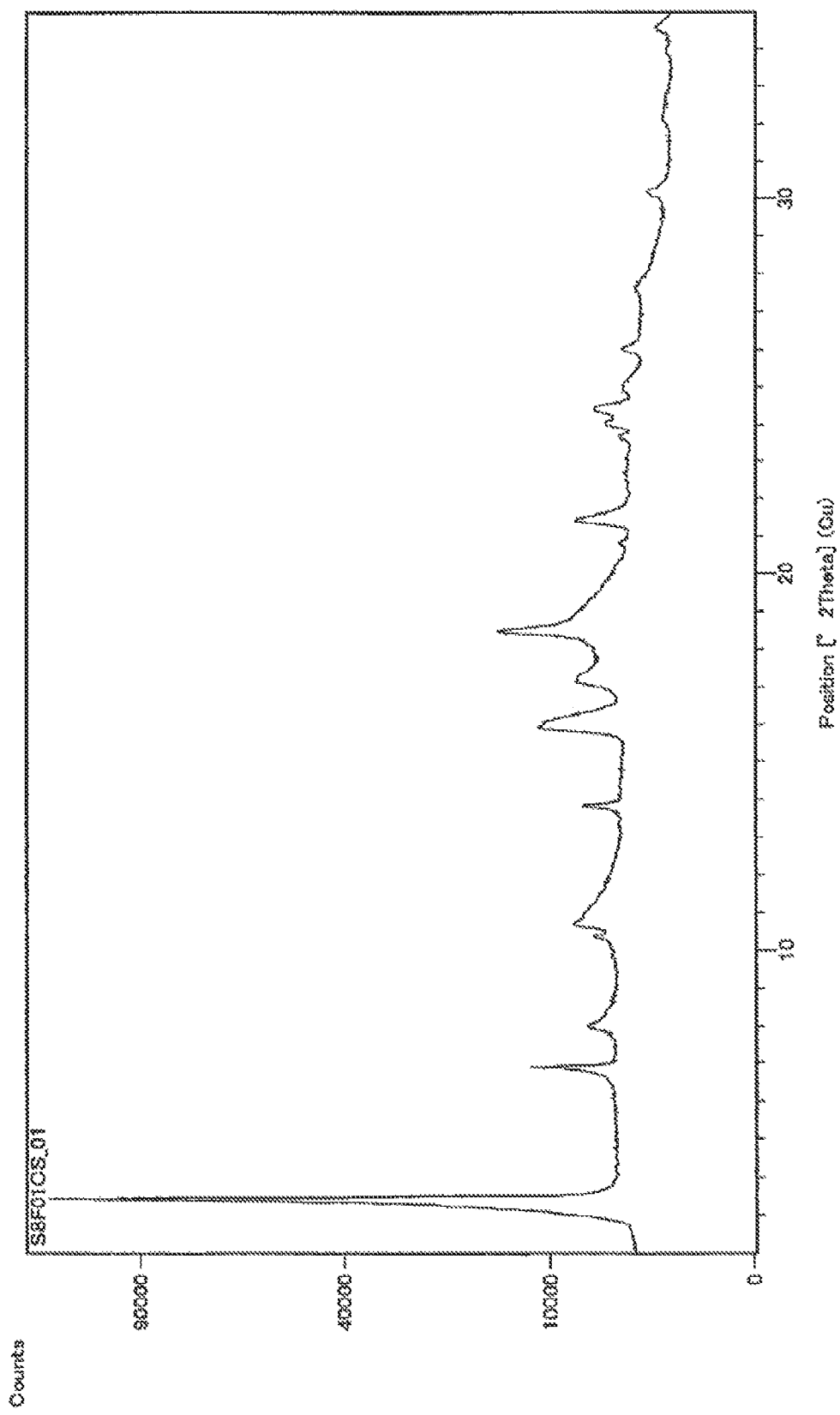
FIG. 3 shows one example of measurement results of powder X-ray diffraction of the monohydrate crystal measured in Test Example 5 (Condition 2).
Figure 4:
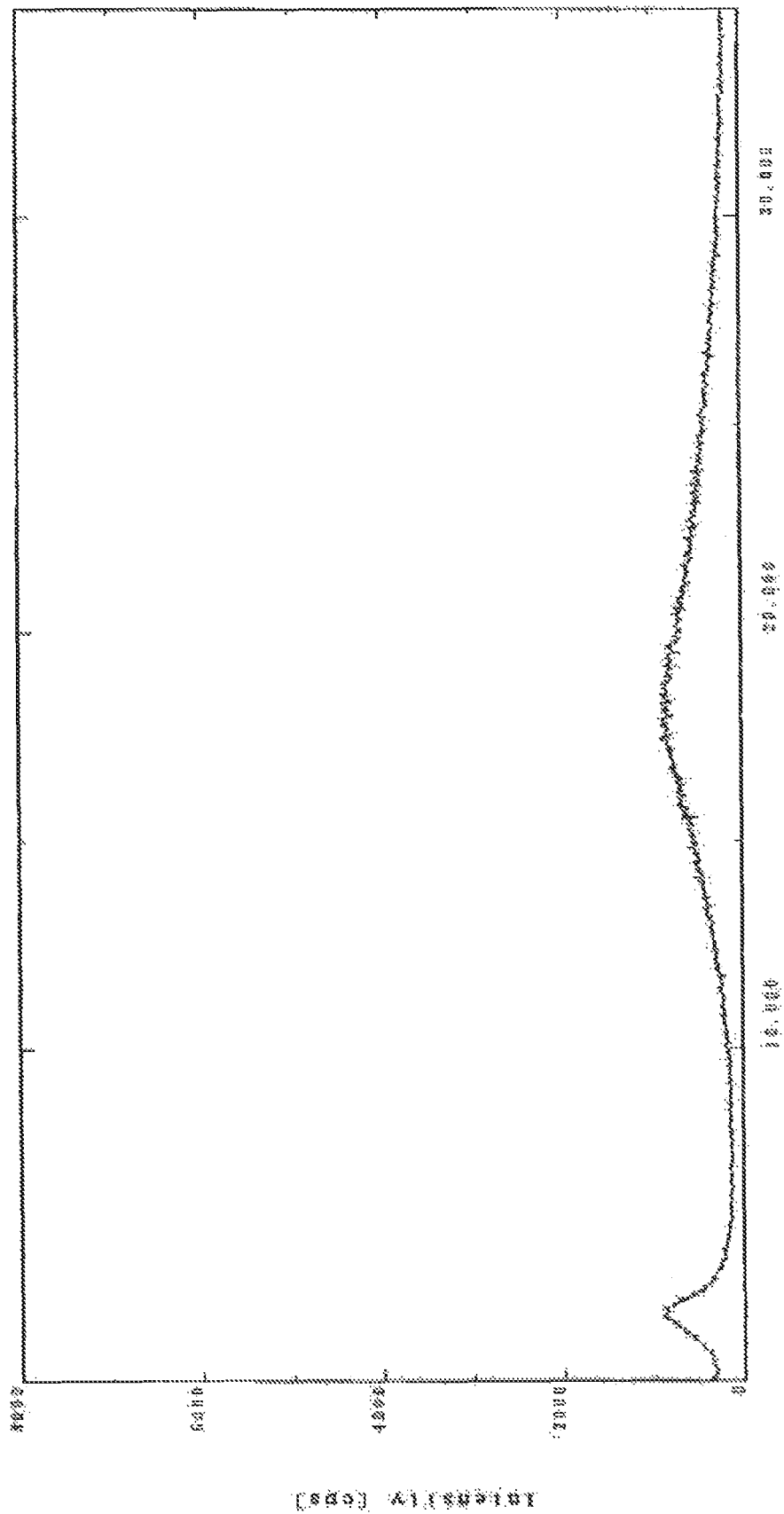
FIG. 4 shows one example of measurement results of powder X-ray diffraction of the amorphous form measured in Test Example 5.
Figure 5:
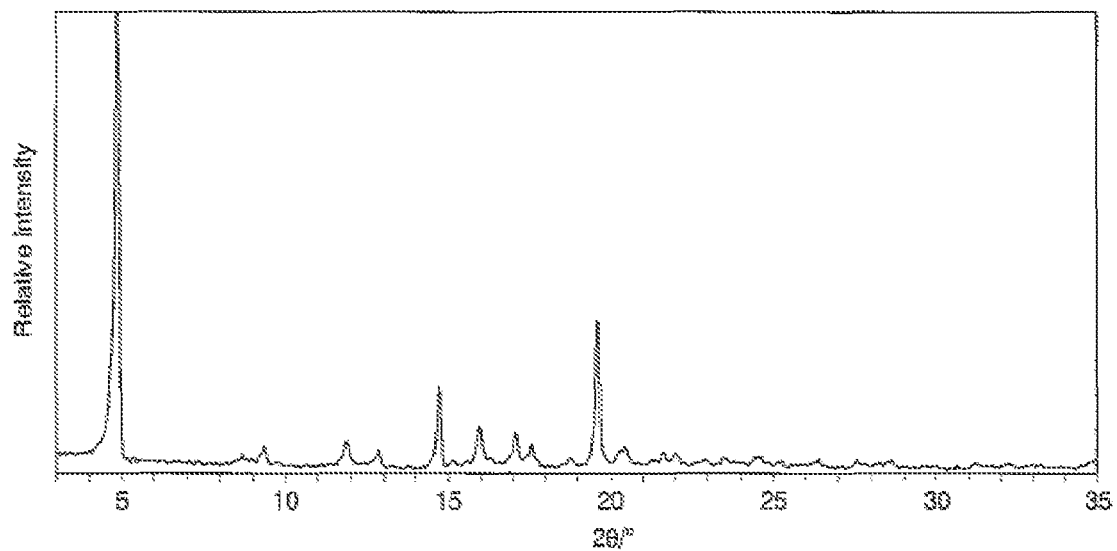
FIG. 5 shows one example of measurement results of powder X-ray diffraction of the co-crystal with sodium acetate measured in Test Example 5.
Figure 6:
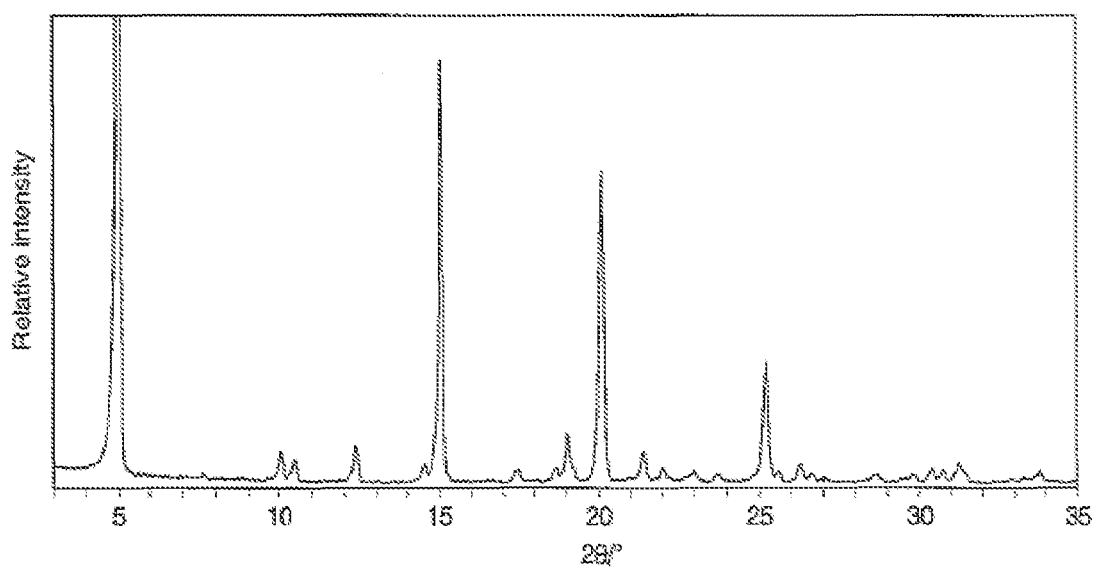
FIG. 6 shows one example of measurement results of powder X-ray diffraction of the co-crystal with potassium acetate measured in Test Example 5.

The result of the monohydrate was shown in FIG. 2. Peaks were observed in diffraction angles (2θ) of about 3.5°, 6.9°, 10.4°, 13.8°, 16.0°, 17.2°, 18.4°, 20.8°, 21.4° and 24.4°. The result of the co-crystal with sodium acetate was shown in FIG. 4. Peaks were observed in diffraction angles (2θ) of about 4.9°, 8.7°, 9.3°, 11.9°, 12.9°, 14.7°, 16.0°, 17.1°, 17.7°, 19.6°, 21.6° and 22.0°. The result of the co-crystal with potassium acetate was shown in FIG. 5. Peaks were observed in diffraction angles (2θ) of about 5.0°, 10.0°, 10.4°, 12.4°, 14.5°, 15.1°, 19.0°, 20.1°, 21.4° and 25.2°.

The invention claimed is:

1. A crystal of a compound represented by Formula (XI):

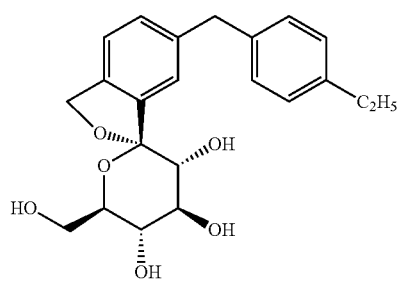

(XI)

which is a monohydrate, and which has peaks at diffraction angles (2θ) of about 3.5 °, 6.9°, and 13.8° in X-ray powder diffraction pattern.

2. The crystal of a compound represented by Formula (XI) according to claim 1, which has peaks at diffraction angles (2θ) of about 3.5°, 13.8°, 16.0°, 17.2°, and 18.4° in X-ray powder diffraction pattern.

3. The crystal of a compound represented by Formula (XI) according to claim 1, which has peaks at diffraction angles (2θ) of about 3.5°, 6.9°, 13.8°, 16.0°, 17.2°, 18.4°, 20.8°, 21.4°, and 24.4° in X-ray powder diffraction pattern.

4. The crystal of a compound represented by Formula (XI) according to claim 1, which is obtainable by crystallization from a solution of the compound in a mixture of acetone and water.

5. The crystal of a compound represented by Formula (XI) according to claim 4, wherein the ratio of acetone:water is 1:3.5 to 1:7 by volume.

6. A process for preparing the crystal of a compound, wherein the compound is represented by Formula (XI):

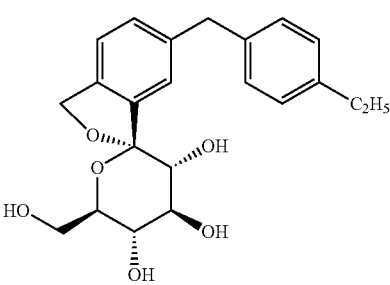

(XI)

which is a monohydrate, and which has peaks at diffraction angles (2θ) of about 3.5°, 6.9°, and 13.8° in X-ray powder diffraction pattern, wherein the process comprises Step a): converting a compound of Formula (XI):

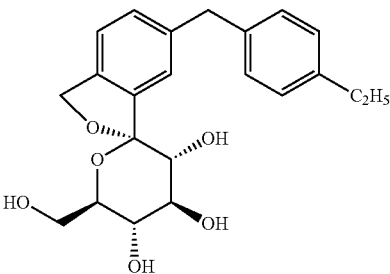 [SMILES: CCc1ccc(Cc2ccc3c(c2)[C@]2(OC3)O[C@H](CO)[C@@H](O)[C@H](O)[C@H]2O)cc1]

to a compound of Formula (Xc):

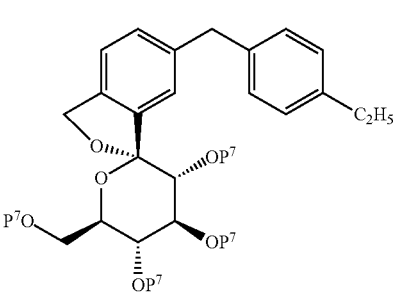

(Xc)

wherein $P^7$ is a protecting group of hydroxy;

Step b): crystallizing the compound of Formula (Xc) and purifying the compound by recrystallization;

Step c): removing a protecting group(s) from a compound of Formula (Xc) to give a higher-purity compound of Formula (XI) than that used as a starting material in step a), and crystallizing the resulting compound to give the crystal of Formula (XI).

7. The process according to claim 6, wherein $P^7$ is selected from t-butylcarbonyl and methoxycarbonyl.

* * * * *